(12) United States Patent
Potthast

(10) Patent No.: US 11,986,563 B1
(45) Date of Patent: May 21, 2024

(54) PORTABLE, SAFE UV HAND AND SURFACE SANITIZER AND METHOD OF USE

(71) Applicant: James William Potthast, Woodstock, IL (US)

(72) Inventor: James William Potthast, Woodstock, IL (US)

(*) Notice: Subject to any disclaimer, the term of this patent is extended or adjusted under 35 U.S.C. 154(b) by 0 days.

(21) Appl. No.: 17/314,981

(22) Filed: May 7, 2021

Related U.S. Application Data

(60) Provisional application No. 63/047,163, filed on Jul. 1, 2020, provisional application No. 63/038,851, filed on Jun. 14, 2020, provisional application No. 63/030,368, filed on May 27, 2020, provisional application No. 63/021,254, filed on May 7, 2020.

(51) Int. Cl.
  *A61L 2/00* (2006.01)
  *A61L 2/10* (2006.01)

(52) U.S. Cl.
  CPC .............. *A61L 2/0047* (2013.01); *A61L 2/10* (2013.01); *A61L 2202/11* (2013.01); *A61L 2202/14* (2013.01); *A61L 2202/16* (2013.01)

(58) Field of Classification Search
  CPC .............. A61L 2/0047; A61L 2202/11; A61L 2202/14; A61L 2202/16
  See application file for complete search history.

(56) References Cited

U.S. PATENT DOCUMENTS 3,970,856 A * 7/1976 Mahaffey ............. A61C 19/004
250/493.1

| | | |
|---|---|---|
| 4,786,812 A | 11/1988 | Humphreys |
| D358,637 S | 5/1995 | Boehme |
| 5,666,410 A | 9/1997 | McLane |

(Continued)

FOREIGN PATENT DOCUMENTS

| | | |
|---|---|---|
| CN | 108785863 A | 11/2018 |
| CN | 110694089 A | 1/2020 |

(Continued)

OTHER PUBLICATIONS

Author: Michael Hemsworth; "Smart Phone Mounted UV-C Santizers"; Published by Trend Setter on Jul. 16, 2020 in Tornto, Canada.

(Continued)

*Primary Examiner* — Sean E Conley

(57) ABSTRACT

A portable, handheld light sanitizer (10) having a skin-surface sanitization mode with safety features for automatically terminating or automatically preventing initiation of a skin sanitization cycle to prevent excessive skin radiation time that could be harmful and preventing radiation that is too intense due to the UV light source being too close to the skin-surface (FIGS. 6-7), and a non-skin surface sanitization mode (FIGS. 6 and 8) which may be unlimited in time duration but in which the UV light source (12) is n ay deenergized if the UV light source (12) is directed at a person's skin is provided in a cellphone configuration (FIGS. 2-5) in which functional elements of a cellphone are also used by the sanitizer functions, a fixed light wand configuration (FIGS. 4-7), flashlight configurations (FIGS. 10-13 and 14-16), a foldable light wand configuration (FIGS. 20-22), a cellphone protector case configuration (FIGS. 26-28) and a cellphone connectable tab configuration (FIGS. 29-31).

32 Claims, 16 Drawing Sheets

(56) References Cited

U.S. PATENT DOCUMENTS

| | | | |
|---|---|---|---|
| D428,503 S | 6/2000 | Rann et al. | |
| 6,132,897 A | 10/2000 | Chen | |
| 6,254,625 B1 | 7/2001 | Resenthal et al. | |
| 6,579,495 B1 | 6/2003 | Maiden | |
| 7,246,920 B1 | 7/2007 | Hopkins | |
| 7,250,615 B1 | 7/2007 | Soong et al. | |
| D581,058 S | 11/2008 | Elkerbout | |
| D629,529 S | 12/2010 | Russell, II et al. | |
| 9,265,850 B2 | 2/2016 | Davis et al. | |
| 9,572,903 B2 | 2/2017 | Dobrinnsk et al. | |
| 9,687,577 B2 | 6/2017 | Dobrinsky et al. | |
| 10,543,290 B2 | 1/2020 | Shur et al. | |
| 10,639,387 B2 | 5/2020 | Bonutti et al. | |
| 10,697,164 B1 | 6/2020 | Al-Sabah et al. | |
| 10,849,995 B2 | 12/2020 | Crosby | |
| 10,940,220 B2 | 3/2021 | Crosby et al. | |
| 2001/0042842 A1 | 11/2001 | Leihhley et al. | |
| 2003/0086831 A1* | 5/2003 | Horton, III | A61L 9/205 250/455.11 |
| 2004/0034398 A1 | 2/2004 | Eckhardt et al. | |
| 2004/0256581 A1 | 12/2004 | Au et al. | |
| 2006/0078484 A1 | 4/2006 | Greep | |
| 2006/0079948 A1 | 4/2006 | Dawson | |
| 2006/0212099 A1 | 9/2006 | Riddell | |
| 2007/0055195 A1 | 3/2007 | Browne | |
| 2008/0253941 A1 | 10/2008 | Wichers et al. | |
| 2009/0196622 A1 | 8/2009 | Shin et al. | |
| 2009/0230321 A1 | 8/2009 | Chen | |
| 2010/0114266 A1 | 5/2010 | Lechtwhaler | |
| 2010/0222852 A1 | 9/2010 | Vasily et al. | |
| 2011/0004280 A1 | 1/2011 | Irwin | |
| 2012/0085927 A1 | 4/2012 | Maeng et al. | |
| 2012/0156094 A1 | 6/2012 | Gordon | |
| 2013/0013932 A1 | 1/2013 | Irwin | |
| 2014/0319374 A1 | 10/2014 | Chandler | |
| 2015/0174426 A1 | 6/2015 | St. Germain et al. | |
| 2016/0030612 A1 | 2/2016 | Kim et al. | |
| 2016/0184467 A1* | 6/2016 | Cheng | A61L 2/10 250/492.1 |
| 2017/0080116 A1 | 3/2017 | Kreiner et al. | |
| 2017/0080117 A1 | 3/2017 | Gordon | |
| 2017/0080251 A1 | 4/2017 | Yehezkel | |
| 2017/0157276 A1 | 6/2017 | Dobrinsky et al. | |
| 2017/0216466 A1 | 8/2017 | Dujowich et al. | |
| 2018/0071414 A1 | 3/2018 | Dujowhich et al. | |
| 2018/0207302 A1 | 7/2018 | Vasilnko | |
| 2018/0343847 A1 | 12/2018 | Ervin | |
| 2019/0070325 A1 | 3/2019 | Preminger et al. | |
| 2019/0099613 A1 | 4/2019 | Estes et al. | |
| 2019/0117802 A1 | 4/2019 | Hishinuma et al. | |
| 2019/0172336 A1 | 6/2019 | Haidegger et al. | |
| 2019/0184044 A1 | 6/2019 | Yellen et al. | |
| 2019/0240369 A1 | 8/2019 | Rotelli | |
| 2019/0255201 A1* | 8/2019 | Rosen | A61L 2/0052 |
| 2019/0326105 A1 | 10/2019 | Matsumoto | |
| 2020/0030469 A1 | 1/2020 | Neister et al. | |
| 2020/0057181 A1 | 2/2020 | Yang et al. | |
| 2020/0069823 A1 | 3/2020 | Pangan, Jr. et al. | |
| 2020/0093030 A1 | 3/2020 | Yamakoshi et al. | |
| 2020/0108160 A1 | 4/2020 | Jung et al. | |
| 2020/0261608 A1 | 8/2020 | Crosby et al. | |
| 2020/0261611 A1 | 8/2020 | Bonutti et al. | |
| 2021/0196848 A1* | 7/2021 | Baarman | H04M 1/18 |

FOREIGN PATENT DOCUMENTS

| | | |
|---|---|---|
| CN | 2105215540 U | 5/2020 |
| CN | 2114342266 U | 9/2020 |
| EP | 2465543 B1 | 1/2013 |
| EP | 3336817 B1 | 10/2019 |
| KR | 20200098104 A | 8/2020 |
| WO | 2016019367 A2 | 2/2016 |
| WO | WO2016019367 A3 | 2/2016 |
| WO | WO2019241112 A1 | 12/2019 |
| WO | WO202000838 A1 | 4/2020 |
| WO | WO2020083851 A1 | 4/2020 |

OTHER PUBLICATIONS

Author; Shaurya Karanbir Gurung; Title: "DRDO innovates automatic sanitizer and ultraviolet devices to fight coronavirus"; Internet Published at least as early as Mar. 30, 2020., by the Economic Times, economictimes.indiatimes.com. Published in India.

Author: Nerd Techy; . Title: "Best Handheld Germicidal UV Light Wand 2020The UVLyzer Sterilizes Any Surface in Mere Monments"; Internet Published at least as early as July at https://nerdtechy.com2020 by Nerd Techy.

* cited by examiner

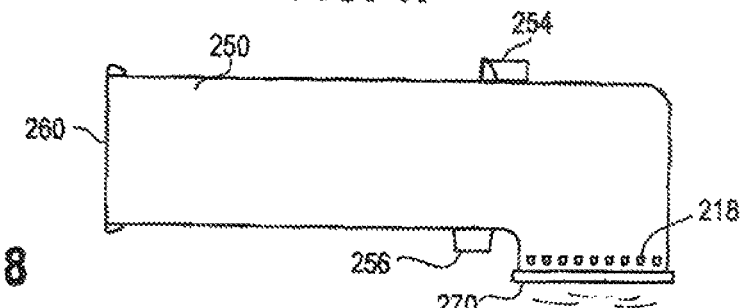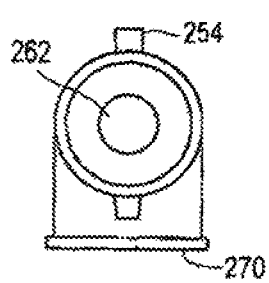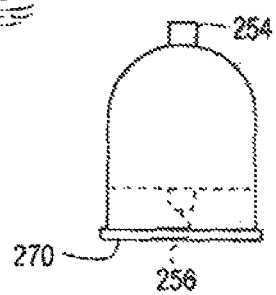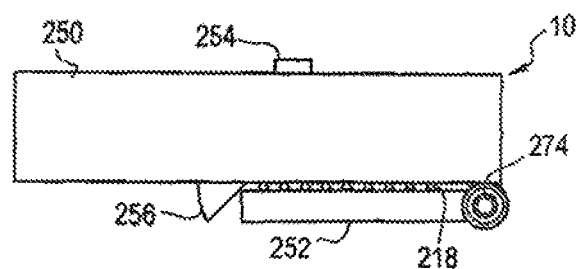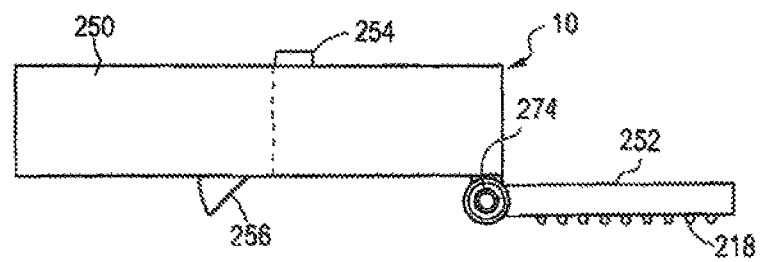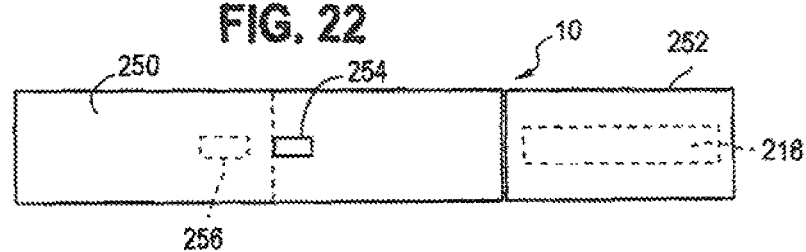

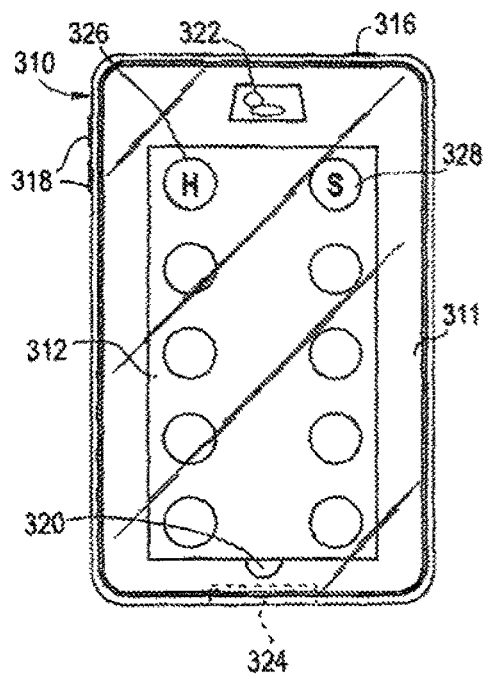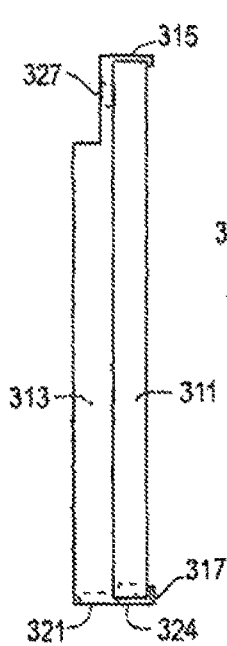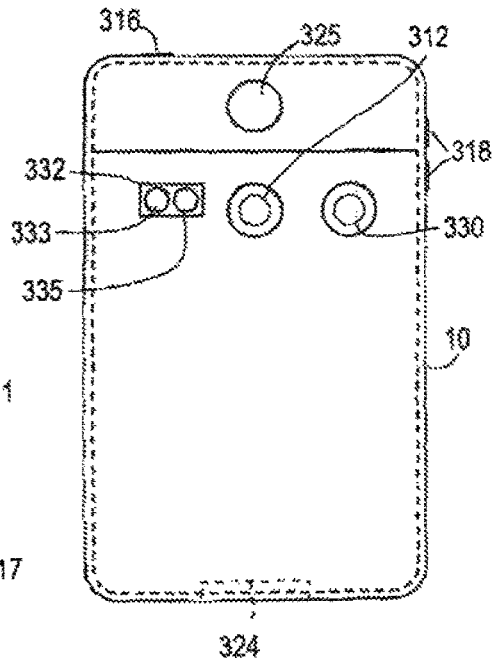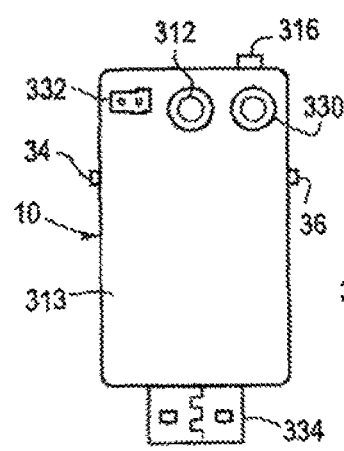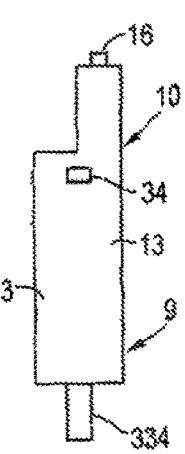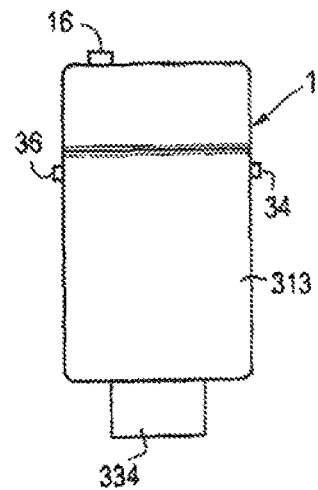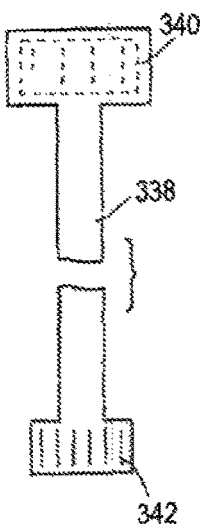

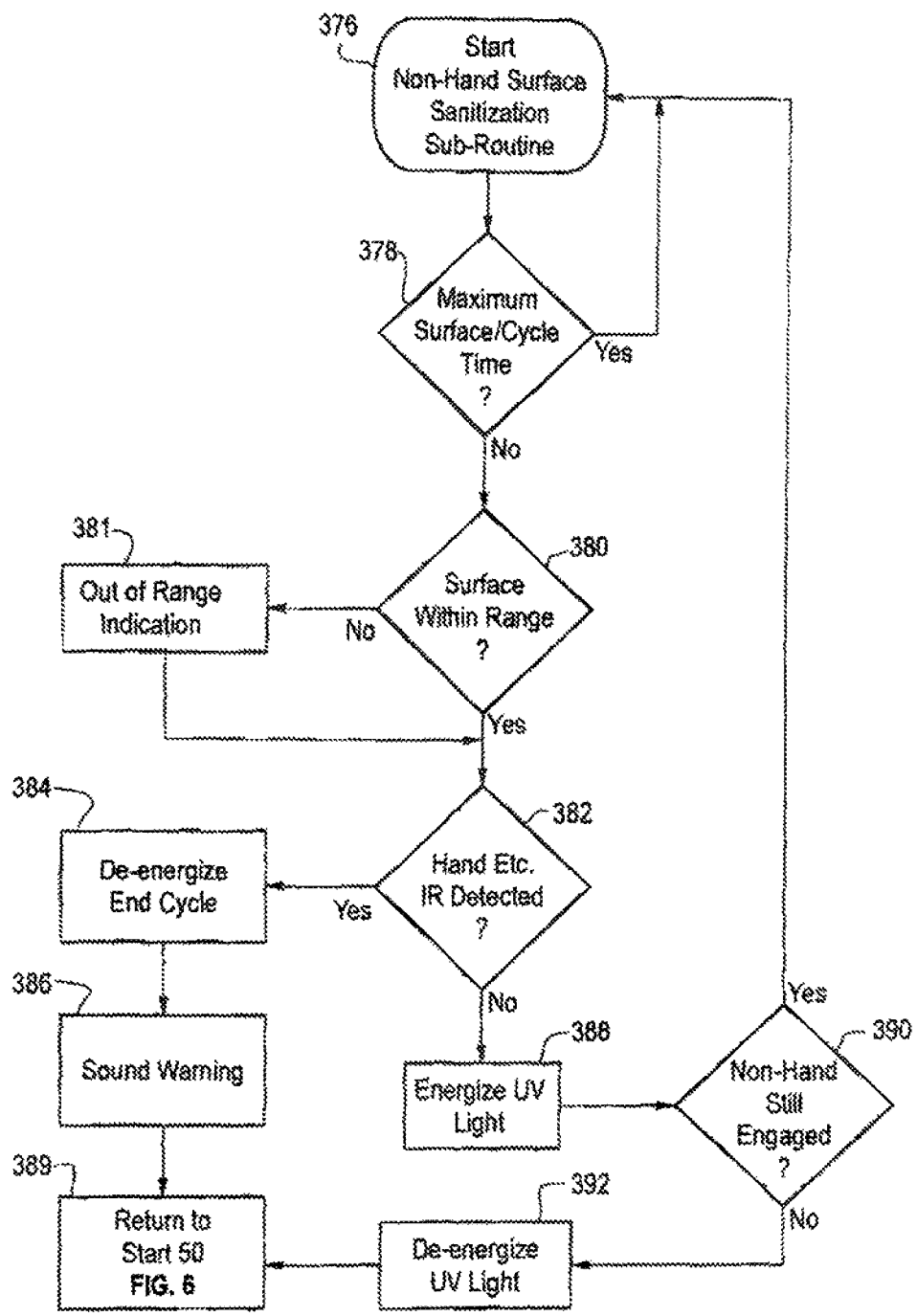

PORTABLE, SAFE UV HAND AND SURFACE SANITIZER AND METHOD OF USE

CROSS-REFERENCE TO RELATED APPLICATIONS

This application claims the benefit under 35 US 119(c) of provisional patent applications: Ser. No. 63/021,254, filed May 7, 2020 and entitled "Personal Handheld, Reusable, Corona Virus UV Hand Sanitizer and Method; Ser. No. 63/030,368, filed May 27, 2020 and entitled "Safe, Portable UV Hand and Surface Sanitizer and Method of Use"; Ser. No. 63/038,851, filed Jun. 14, 2020; and Ser. No. 63/047,163, filed Jul. 1, 2020 and entitled "UV Hand and Surface Sanitizer Interfaceable with a Cellphone and Method of Use", all of which are hereby incorporated by reference.

BACKGROUND

Field of the Invention

This invention generally relates generally to ultraviolet light sanitizers, and more specifically, to portable ultraviolet light sanitizers.

Discussion of the Prior Art

It is well known that UV radiation has a deleterious effect upon viruses, bacteria and other microscopic infectious organisms, or pathogens. Specifically, short wave ultraviolet light, or UV-C light (200-280 nm) kills or disables microorganisms by disrupting the DNA of bacteria, virus and other pathogens to destroy their ability to multiply and cause disease. Consequently, there are many UV light generating devices that are used for sanitizing, or sterilizing, surfaces. Particularly, there are many portable, hand-held, UV sanitization used to ultraviolet light radiate surfaces spaced from the person.

Examples of such portable ultraviolet radiation devices are shown in U.S. Pat. No. 6,579,495 issued Jun. 17, 2003 to Maiden; U.S. Pat. No. 5,900,212 issued May 4, 1999, to Maiden et al., all of which and the patents cited therein, are hereby incorporated by reference. Other examples of portable UV radiation devices are shown in Published U.S. patent applications 2015/0359915 of Farren et al. published Dec. 17, 2015; 2004/0256581 of Au et al. published Dec. 23, 2004; 2006/0079948 of Dawson published Apr. 13, 2006; 2007/0055195 of Browne published Mar. 8, 2007; and 2016/0184467 of Cheng et al. published Jun. 30, 2016, all of which, and the patents cited therein, hereby incorporated by reference.

While portable, many of these sanitization devices are designed to be handled only intermittently in an office, medical facility or other like workplace location. Generally, they are not of a size, weight or configuration to be easily carried continuously throughout a user's day. Typically, the device rests on a desk or the like and is only picked up when it is desired to sanitize a nearby surface.

More importantly, with reference to the current invention, even if carried by a user to sanitize suspect surfaces they may encounter while traveling, these devices are generally designed solely for use on surfaces remote from a user's hand. Although they could also be used to radiate a user's hand, they are ill-adapted to do so safely. Accordingly, in some of these portable UV sanitization devices, special care is taken to avoid radiation of the skin of a user under any circumstances.

Some known UV light sanitizer are solely intended for use to disinfect a person's hand are not portable and are not well adapted to be made portable. They require a fixed AC power supply, are fixedly mounted to a wall or floor and are too heavy and cumbersome to carry from place to place. For example, in Published U.S. patent application 2019/011780 of Hishinuma et al. published Apr. 25, 2019, a hot air hand dryer incorporates a UV disinfection device. The hand dryer is fixedly attached to a wall, is not portable and is not designed to be carried in a user's hand and used at locations spaced from the hand dryer. Since these devices are intended to be used only successively by different persons who must come to the fixed location of the sanitizer, there is little risk of any single person being injured due to excessive use. Accordingly, these devices have nothing to prevent excessive use.

A portable, handheld UV light sanitizer is shown in U.S. Pat. No. 10,849,995 issued Dec. 1, 2020 to Crosby which may be held in a hand while being sanitized but due to the size, shape and configuration of the housing unsafe UV light leakage beyond the user's hand is not prevented. It appears that no provision is made to prevent excessive and thus unsafe radiation of the user's hand. Disadvantageously, this hand sanitizer may only be used to sanitize the user's hand and no other surfaces spaced from the sanitizer. A further problem is that due to the configuration of the housing and placement of the UV light sources, radiation is not uniformly distributed across a user's had when holding the sanitizer housing.

Generally, it is believe that all of the known portable UV hand sanitizers suffer from one or more defects that do not adequately protect the user from excessive and thus damaging radiation of a user's skin and are not suitable for both hand sanitizing and sanitization of non-skin surfaces spaced from the user's hand. Accordingly, sanitization can only occur after a user has already touched a pathogen coated surface and possibly already passed the pathogens to other parts of the user's body that may have been touched.

During the Covid-19 pandemic, available personal liquid hand sanitizers can quickly be used up and may not be easily replaced due to scarcity in the market because of and hording or excessive demand exceeding production and distribution capacity. Even when the pandemic is over, such personal liquid hand sanitizers, may once again become scarce if another virus arises or the Corona-19 virus or if a variant returns.

Accordingly, during this time of corona virus pandemic and shortages of liquid hand sanitizers, there is an urgent need to provide an alternative and convenient means that a person can carry to sanitize their hands after touching a surface, such as a door knob or grocery item suspected of harboring dangerous pathogens. A sanitizer is needed that is convenient to carry and can easily be used to sanitize a person's hands immediately after touching door handles, food items, another person's hand and other like surfaces that one may routinely and necessarily touch and which may be covered with dangerous microscopic virus and the like. There is also a need for a person to be able with the same device to sanitize a suspect surface prior to touching the surface to increase the chance of avoiding any infectious contact, whatsoever, with pathogenic viruses or bacteria.

SUMMARY OF THE INVENTION

It is therefore an object of the present invention to provide a safe portable UV light hand sanitizer that is convenient and easy for a person to easily and conveniently carry with them and use to both sanitize a suspect surface prior to touching the surface and also to safely sanitize a user's hands after they have touched a suspect surface.

More specifically, it is one object of the present invention to provide a UV hand sanitizer that is eminently portable, convenient and which most people will always carry and have with them when a need arises to sanitize either their hands or a non-skin suspect target surface. More specifically, it is an object to provide such a personal sanitizer with means to prevent excessive use on the hand of a single user that might be harmful.

A further objective of the invention is to provide personal, portable UV light sanitizer, with a sanitizer housing having surrounding, enclosing walls including a back wall and a front wall and being of a size enabling easy carry by one hand of a user, a portable, rechargeable electrical power source, a source of UV light mounted to the housing, for radiating a target surface spaced from the housing at which it may be directed, with sufficient intensity to kill or otherwise disable any pathogenic viruses or bacteria that may be on the target surface, if and when the target surface is within a maximum effective distance range of the UV light source, an energization switch for connecting the portable power source to the UV light source, means for sensing at least one characteristic of the target surface at which the UV light source is directed, a user control switch, a microprocessor controller powered by the portable power source for controlling the energization switch to selectively energize the UV light source with the power source in response to the user control switch, and in automatic response to the at least one characteristic of the target sensed by the target characteristic sensing means Preferably, one characteristic of the target is the distance from the UV light source to the target as determined by a range finder for automatically determining the distance to the target at which the UV light source is directed and another characteristic is whether the target is radiating infrared radiation indicative that the target is a person's skin. If the target is recognized as a person's skin and that it is too close to the UV light source to be safely radiated, energization of the UV light source is automatically terminated.

Yet, another objective of the invention is to provide a method for a user to safely use UV light radiation to reduce the risk of infection from pathogenic viruses or bacteria that may be on a suspect surface that a person wishes to touch or has touched, by performing the steps of carrying a single hand-holdable personal UV sanitizer with a UV light source actuatable by the user in either a non-skin surface sanitization mode with a skin-surface sanitization safety measure to prevent intensity of UV radiation of a person's skin, or a skin surface sanitization mode with safety features to reduce the risks of excessive radiation of a user's skin due to excessive radiation time, prior to touching any suspect non-skin surfaces, actuating the UV light source in the non-skin surface sanitization mode to selectively radiate said suspect non-skin surfaces with sufficient intensity to kill or disable the pathogens that may be harboring on said non-skin target surfaces, and after touching any suspect non-skin surfaces with a user's hand, actuating the UV light source in a skin surface sanitization mode to radiate the user's hand.

A further objective is to provide a method of sanitizing a surface with a personal, portable, hand-held UV light sanitizer, by performance of the steps of directing a UV light source of the sanitizer at a target surface to be sanitized, selectively energizing the UV light source to radiate the target surface with UV light radiation, sensing a target distance signal from the sanitizer indicating whether the target surface distant for the UV light source for the radiation intensity at the surface to be of sufficient strength to kill or disable pathogenic viruses or bacteria on the target surface, and responding to the target distance signal as necessary to locate the UV light source sufficiently close to the target surface to ensure that the radiation intensity is sufficient to kill or disable pathogenic viruses or bacteria on the target surface.

One more object of the invention is to provide a method of safely sanitizing a non-skin surface with a personal, portable, hand-held UV light sanitizer, by performance of the steps of energizing a UV light source to radiate a surface at which the UV light source may be directed, sensing with an infrared light sensor if the UV light source has been inadvertently directed at a skin surface, and automatically deenergizing the UV light source in response to skin surface sensing means sensing that the UV light source is directed at a skin surface.

Still, another objective of the invention is to provide a method of safely sanitizing a user's skin with a personal, portable hand-held UV light sanitizer by performing the steps of initiating energization of a UV light source while directed at a user's skin to radiate the use skin with UV light radiation, automatically terminating energization of the UV light source after a preselected maximum sanitization cycle time period, and automatically preventing energization of the UV light source whenever the total radiation time during a prior preselected prior time period exceeds a preselected maximum safe total radiation time.

While the invention is embodied in several different configurations, since most people carry their cell phone whenever they leave their homes, the present invention may incorporate a cellular telephone, such that the need for a user to remember to carry another device or to carry another device for UV sanitizing will be eliminated. Alternatively, the sanitizer may be configured as a protective backing for a cellphone that is not already equipped with the sanitizer of the present invention. In addition to having all the usual elements of a cellular phone, or cellphone, and being able to perform all the usual functions of a cellphone, the safe UV sanitizer of the present invention also includes one or more a UV LEDs mounted to the back and means for controlling the UV LED to radiate a person's hand or a remote non-hand surface, safely.

In addition, the sanitizer uses a visible light LED, otherwise used to take flash photographs, to illuminate a target surface being radiated with UV sanitizing light to visibly highlight and thus help to visually identify the target at which the UV with radiation is being directed. Similarly, in the case of a cellphone that is incorporated into the sanitizer of the cellphone protective backing configuration, a range finder may be used alternatively by a cellphone camera for purposes of automatic focus and by the sanitizer to ascertain the distance to the target being sanitized to prevent excessive UV radiation when in a skin sanitization mode or to avoid attempting to radiate a non-skin surface from too great a distance to be effective.

Other forms of the sanitizer are embodied in flashlight configurations, fixed and foldable wand configurations, and a small housing configuration attachable to the battery recharging and communication port of a cellphone.

This invention is related to U.S. patent application Ser. No. 17/246,675 of the present inventor filed May 2, 2021, and entitled "Personal, Portable, Handheld UV Sanitizer, and Method of Use", which is hereby incorporated by reference.

BRIEF DESCRIPTION OF THE DRAWING

The foregoing objects, features and advantages will be described in detail and further objects, features and advantages will made apparent from the following detailed description that is given with reference to the following figures of the drawing, in which:

FIG. 17 is a side elevational view of another flashlight like configuration of the safe UV sanitizer of FIG. 9 UV light radiation flash light is directed laterally outward from a cylindrical body;

FIG. 18 is an elevational view of a back end of the safe UV hand sanitizer of FIG. 17;

FIG. 19 is an elevational view of a front end of the safe UV hand sanitizer of FIG. 17;

FIG. 20 is a side elevational view of another configuration of the safe UV hand sanitizer of FIG. 9 in which a UV light wand is pivotal mounted to one end of a housing and collapsed against the housing to shorten the sanitizer during carry and to protect the UV light;

FIG. 21 is another side elevational view of the safe UV hand sanitizer of FIG. 20 in which the UV light wand is in an extended operative position for use;

FIG. 22 is a top, or plan, view of the safe UV hand sanitizer of FIG. 21;

FIG. 26 is an elevational front view of a cellphone to which a celiphone protector configuration of the UV sanitizer is attached;

FIG. 27 is a side elevational view of the cellphone attachable UV sanitizer of FIG. 26;

FIG. 28 is a back view of the cellphone attachable UV sanitizer configuration of FIG. 26;

FIG. 29 is a back elevational view of a cellphone attachable tab configuration of the sanitizer of the present invention which can be releasably attached to a USB port of a cellular telephone;

FIG. 30 is a side elevational view of the cellphone attachable tab configuration of the UV sanitizer of FIG. 29;

FIG. 31 is a front elevational view of the cellphone attachable UV sanitizer of FIGS. 29 and 30;

FIG. 32 is a plan view of an extension cord to remotely connect the UV sanitizer of FIGS. 29-31 to a cell phone; FIGS. 34, 35 and 36 form a composite logic flow chart of the control software for both the hand sanitize and the non-hand surface sanitize functions of the present invention.

DETAILED DESCRIPTION

Figure 1A:
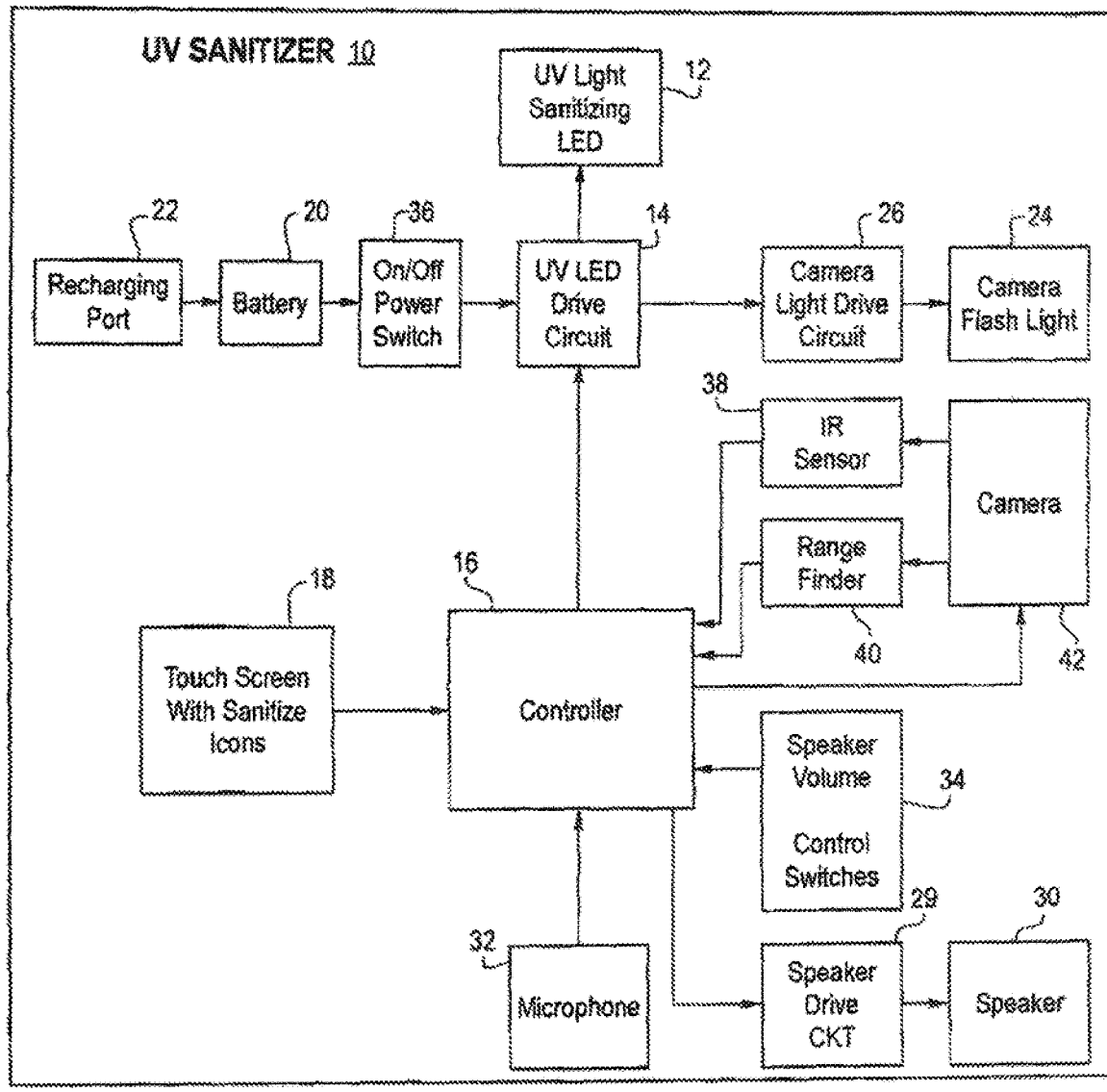
FIG. 1A is a functional block diagram of a preferred embodiment of the safe 6 UV sanitizing cellular phone of the present invention.

Referring to FIG. 1A, one form of the present invention incorporates UV light sanitization functions into a cellular telephone, or cellphone, and employs some of the conventional cellphone features to assist in the performance of the UV light sanitization functions to form a UV sanitizer, or UV sanitizing cellphone, 10.

Figure 2:
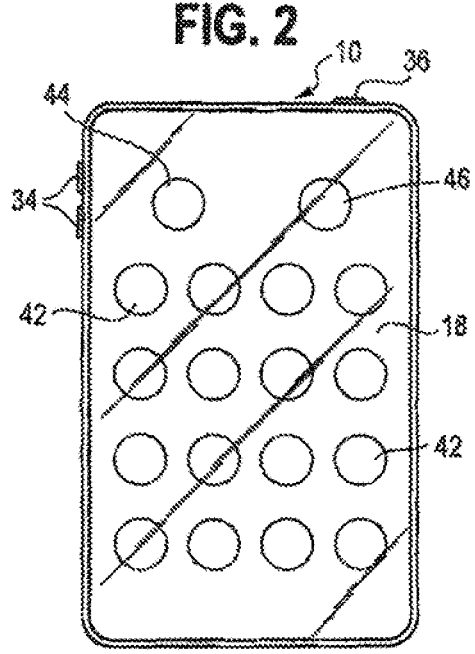
FIG. 2 is a schematic front elevational view of the sanitizing cellular phone of FIG. 1, illustrating a touch screen with various icons for selection of different phone features and also including two icons for selection of the hand sanitizing function and the non-hand surface sanitizing feature of the UV sanitizing cellular telephone.
Figure 3:
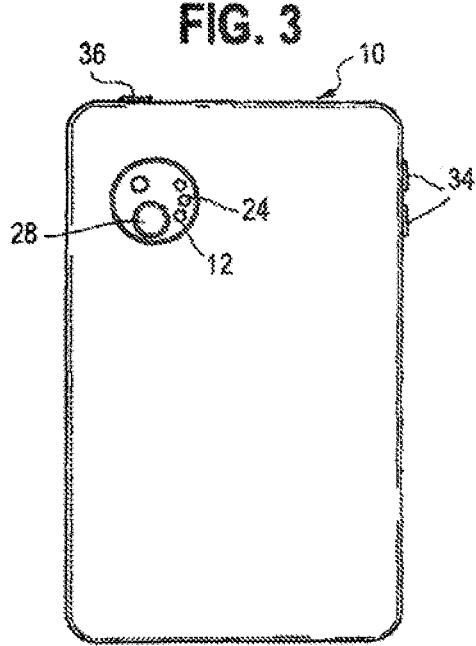
FIG. 3 is a schematic back elevational view of the safe UV sanitizing cellular telephone of FIGS. 1 and 2 and illustrating the location of the ultraviolet light source used for sanitization, the camera lens and lens cover and light ports of the IR sensor of FIG. 1A.

The portable, safe UV sanitizer 10 of the present invention, unlike known UV light sanitizers, is contained within, or carried by, the housing of a cellular telephone, or cellphone, such as illustrated in FIGS. 2 and 3 and uses some of the cellphone features to perform sanitization functions, as described in detail below.

As explained in greater detail below, a single rechargeable electrical power source is used to power both cellphone and sanitization functions; the range finder of a cellphone camera is used to properly distance a target surface from the UV light source sufficiently close for the radiation intensity at the target surface is sufficient to disable infectious pathogens and to prevent possibly injurious high levels of radiation intensity on a person's skin; a single microprocessor is programmed to control both cellphone functions and UV light sanitization functions; a lens of the cellphone camera may be used to focus skin indicative infrared radiation onto an infrared skin sensor; a visible light source used for flash photography is also employed to illuminate and thus highlight UV radiation targets; and the touch screen is provided with UV light sanitization icons for user initiation of UV light radiation in either a skin-sanitizing mode of operation or a non-skin surface sanitizing mode of operation. mode.

Unlike all known cellphones, the sanitizing cellphone 10 has an ultraviolet lamp, preferably one or more UV LEDs 12 facing outwardly from the back of the housing, as illustrated in FIG. 3, described below. Under control of the user, the UV LED 12 may be used to UV sanitize a user's hand or a non-hand surface, such as a door handle, food item, etc. Although, other UV light frequencies could be used to sanitize surfaces, preferably the UV LED operates to produce UV-C light waves, wavelength 200-280 nm., which are believed to be optimum for killing or otherwise disabling corona viruses, such a COVID-19, other viruses, infectious bacteria, and other possibly dangerous infectious microorganisms.

The length of time that a pathogen must be radiated with the UV light to be disabled depends upon the intensity of the UV light where it impinges the target surface. Both the optimum radiation time and intensity needs to be determined empirically or from available results of UV light sanitization scientific studies and may vary for different infectious microorganism. Within a median range, the greater the intensity, the shorter the time needed to sanitize and vice versa. As a matter of convenience of use, the maximum time duration should be less than ten seconds. The UV light may radiate from the back of the sanitizer housing 11 with a predetermined fixed configuration or it may be variably focused into a beam of greater or lesser width.

In order for an entire hand to be radiated it must be located a minimum distance from the cell phone. If the hand is too close, then the light will impinge only a part of the hand with full intensity which may be potentially damaging in addition to being ineffective to sanitize any part of the hand which is not being radiated. Otherwise, if the hand is too far away from the light the light may be too spread out and thus too weakened to kill or disable pathogens on the hand. An adjustable or nonadjustable lens may be provided to sharpen or widen the light being admitted by the LED light source.

Additionally, in accordance with one aspect of the invention, means are provided to assist the user to locate their hand at an optimum distance from the source of the UV radiation and to thereby prevent failure to sanitize or damage to a user's hands due to concentrated UV radiation on the only one part of a user's hand. Preferably, the distance range is approximately six to ten inches, but this distance should be determined empirically once the initial radiation intensity of the LED is determined. Also, some UV LED's are more efficient than others and thus the light energy may vary even if the input energy remains the same.

As noted, the intensity of the radiation on a hand or surface, in addition to depending upon the intensity of the light as it leaves the LED 12, also depends upon the distance between the LED 12 and the surface being radiated. The farther the LED is from the hand or suspect surface, the weaker will be the intensity of the radiation on the surface, and vice versa. If target distance is too close, then the intensity may be too great and cause possible injury to a hand. If the target distance is too great, then the intensity may be insufficient to kill the viruses, etc.

While the user may be provided with operating directions with respect to the optimum, maximum and minimum distances, in accordance with the present invention, a range finder 40 is provided to determine the distance to which the sanitizing LED 12 may be from the target when the LED is being actuated. The controller 16 responds to signals from the range finder 40 to control the LED, increasing or decreasing drive or turning the LED off if too close to a person's hand or providing distance information. The distance information may be provided to the user via a speaker 30 indicator lights or images appearing on the touch screen 18. For example, an audible warning message, such as "Too close!" may be provided. Alternatively, an indicative message or other image may be displayed on the touch screen providing an indication of range status.

While there is no danger in locating the light to close to a non-skin target surface, preferably, the range finder 40 is also used when the cellular phone 10 is being used to sanitize a non-hand surface to make sure that the surface is not too far away for effective sanitization. The use of range finders in autofocus cameras have been used for many years, but the preferred type of range finder is one that is coupled to the focus mechanism so that the lens is focused correctly when the rangefinder aligns duplicate images. Such optical range finders are commonly used with both cellphone cameras freestanding cameras having a variable focal range or zoom feature.

In the hand sanitizing cell phone 10 of the present invention, the range finder 40 advantageously performs dual functions of both focusing and detecting distance to a user's hand or a remote non-hand surface. The range finder needs two spaced ports transmission and receipt of laser light. Referring to FIG. 3, if the image from the camera is not used for the range finder, then two ports 47 and 49 are located either behind the camera lens cover or elsewhere on the back of the phone.

Figure 1B:
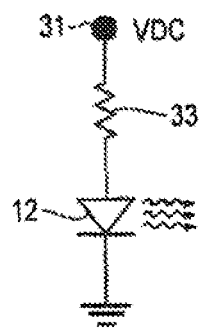
FIG. 1B is a circuit schematic of drive circuit for the UV LED 12 of FIG. 1A.
Figure 1C:
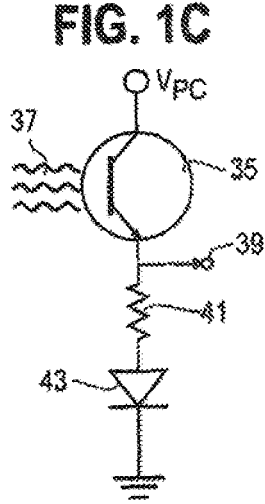
FIG. 1C is a circuit schematic of the IR sensor of FIG. 1A

In addition, when in the non-hand surface sanitizing mode, an infrared, or IR, sensor 38 receiving light through the lens of the camera 42 will sense the presence of the user's face and immediately turn off the UV LED to prevent damage to the user's eyes or facial skin. Referring to FIG. 1C, one simple form of IR sensor has an IR sensitive phototransistor 35 which receives IR light 37 from a person's hand or face when the camera 42 and UV LED light are directed at a person's hand or face. When this occurs, the phototransistor turns on to pass current through a load resistor 41 and isolation diode 43 to generate an indicative signal [is generated on] output 39 to which the controller responds by turning off the UV LED 12. Other IR sensing cameras are shown in U.S. patent application 2019/0364227, filed November, 2019 by McManus et l., which is hereby incorporated by reference, and many other IR detector related devices found in the patent art.

The UV LED drive circuit 14 is controlled by a universal controller 16 that also functions to interface and control all the usual elements of a cellular telephone. The LED drive circuit 14, may provide an electrical drive signal that yields a fixed level of input power to the LED 12 whenever actuated. A suitable drive circuit 14 is shown in FIG. 1C. Whenever the controller 16 detects that one of the icons 44 or 46 of FIGS. 4 and 5 has been touched actuated, a switch (not shown) is caused to connect power to input 31, FIG. 1B of the drive circuit to energize the LED 12. The voltage of the battery 20 may be approximately 5 VDC and the value of the current limiting resistor 33 is selected based on the value of the input voltage to provide an optimum current through the UV LED 12.

Other drive circuits are known which may be suitable for use in this application, such as shown in one or more of U.S. Pat. No. 10,433,381 issued Oct. 1, 2019 to Sakai et al. and 10,582,577 issued Mar. 3, 2020 to Zhao et al. and US. Patent applications 20202019/0053848 filed Oct. 22, 2019, by Lai et al. and 2020/0120768 field Jun. 15, 2019 by Lin et al., all of which and the patents cited therein being are hereby incorporated by reference. Referring to one form of the drive circuit 16 shown in FIG. 2, preferably, the UV light 18 is one or more UV LED's 19, and the voltage of the battery 22 may be approximately 5 VDC. The value of the current limiting resistor 33 is selected based on the value of the input voltage to provide an optimum current through the UV LED 12.

Alternatively, the drive circuit 14 can provide a drive signal of varying input power in response to signals from the controller 16 by varying the resistance of the current limiting resistor 33 to increase or decrease the radiation intensity based on the distance from the target as determined by the range finder 40.

The other features and elements of a customary cellular telephone includes a rechargeable battery 20 connectable with charging port 22 to the UV LED 12 that is used not only for powering the customary functions of the camera 42 but also for powering the UV sanitization elements. The customary elements include a camera flash light 24 connected to the battery 20 through a camera flash interface circuit 26, a camera lens 28, a speaker 30 driven by a speaker drive circuit 29 connected to a microphone 32, speaker volume control switches 34 and a power on-off switch 36. A radio signal transmitter 19 and a radio receiver 21 and associated antenna (not shown) enables conventional cellphone voice and message communication and access to the internet. Reference should be made to the plethora of patents relating to cellular telephones if further details are needed with respect to the normal and customary functions of a cellphone.

Figure 4:
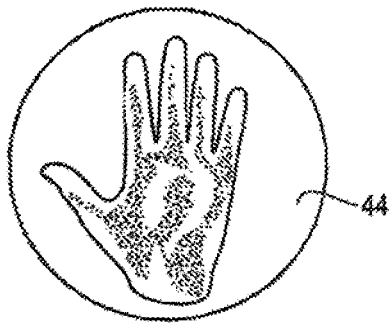
FIG. 4 is a schematic illustration of the UV hand sanitize function selection icon of FIG. 2.
Figure 5:
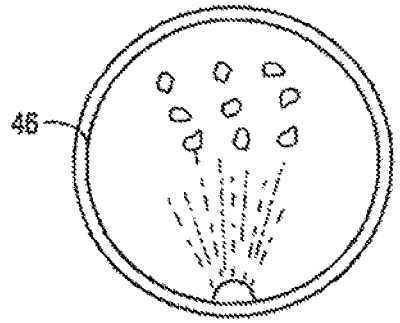
FIG. 5 is a schematic illustration of the non-hand, surface sanitization function selection icon of FIG. 2.

Referring to FIG. 2, in addition to the customary icons, in accordance with the present invention two other unique icons 44 and 46, respectively shown in FIGS. 4 and 5. The icon 44 of FIG. 4 preferably has a fanciful depiction of a hand, perhaps with small dots representing infectious microorganisms. If this icon is momentarily pressed or touched by a user of the phone to sanitize the user's hand, then, if the hand is detected by the range finder 40 to be at a suitable distance from the phone 10, the controller causes a hand sanitize cycle to be initiated in which the LED is turned on but the time that it is on and the intensity are automatically limited to ensure safety.

Should the hand be detected out of range by the range finder 40, then the LED will be automatically be turned off and the user will have to start a new cycle to sanitize their hand. Alternatively, the user is given an appropriate distance warning and allow a short time to make correction.

The UV LED light source may be controlled to automatically turn back on if the user moves their hand back into range, but sanitization depends not only upon the intensity of the radiation but also on the time duration of continuous radiation. A radiation cycle with a fixed total amount of time of radiation that is paused and then is restarted sometime later would possibly allow the pathogens to recover and reduce the effectiveness of such an intermittent hand sanitization cycle. Accordingly, in accordance with the present invention, a restart of the hand sanitization cycle is preferred once interrupted due to the user's hand being out of range. The restart can then result in a full uninterrupted period of UV radiation. The restart is preferably achieved by the user touching the hand sanitization icon again.

The method of use of the present invention includes the concept of training a user to locate their hand at the correct distance from the camera for optimum results by virtue of a number of initial failed attempts in which the LED is automatically turned off due to the hand being out of range.

In addition to the time for a single cycle of hand sanitization being automatically limited, preferably the controller stores and keeps a running total of the number of hand cycles performed in a past preselected time period, such as two hours, and automatically prevents performance of another hand sanitization if the number of hand sanitization cycles exceeds a preselected maximum number during the preselected time period indicating excessive use deemed to be possibly unsafe.

A running total is kept, so that after a period of time has passed without any sanitization cycles have been run, a new hand sanitization may again be initiated. In such case, an audio message or visual message or other visual indication on the touch screen 18 why a new hand sanitization cycle cannot be initiated and advising of when sufficient time has passed to resume use of the hand sanitization function.

Again, the method of the present invention contemplates that successive denials of operation of the hand sanitization cycle due to excessive cycles during a given preselected period will result a teaching or conditioning a user not the perform to excessive cycles over to short of a time to be safe.

The icon 46 of FIG. 5 contains a fanciful depiction of a collection of dots representing microorganisms being radiated with light represented by dashed lines emanating in a radial pattern from a single point. Because inanimate surfaces are not going to be injured or damaged by UV light, there is no absolute need to limit the duration of the radiation, and the LED may be kept energized for as long as the user keeps pressing the surface sanitization icon. Preferably, an audio signal may be provided after preselected time period long enough to generally be sure that a surface has been sanitized based on the distance from the suspect target surface, as determined by the range finder 40.

While not needed for purposes of safety, the LED light 12 is preferably turned off automatically after another preselected time period to save battery power in the event the LED is being kept activated inadvertently or grossly excessively.

Figure 6:
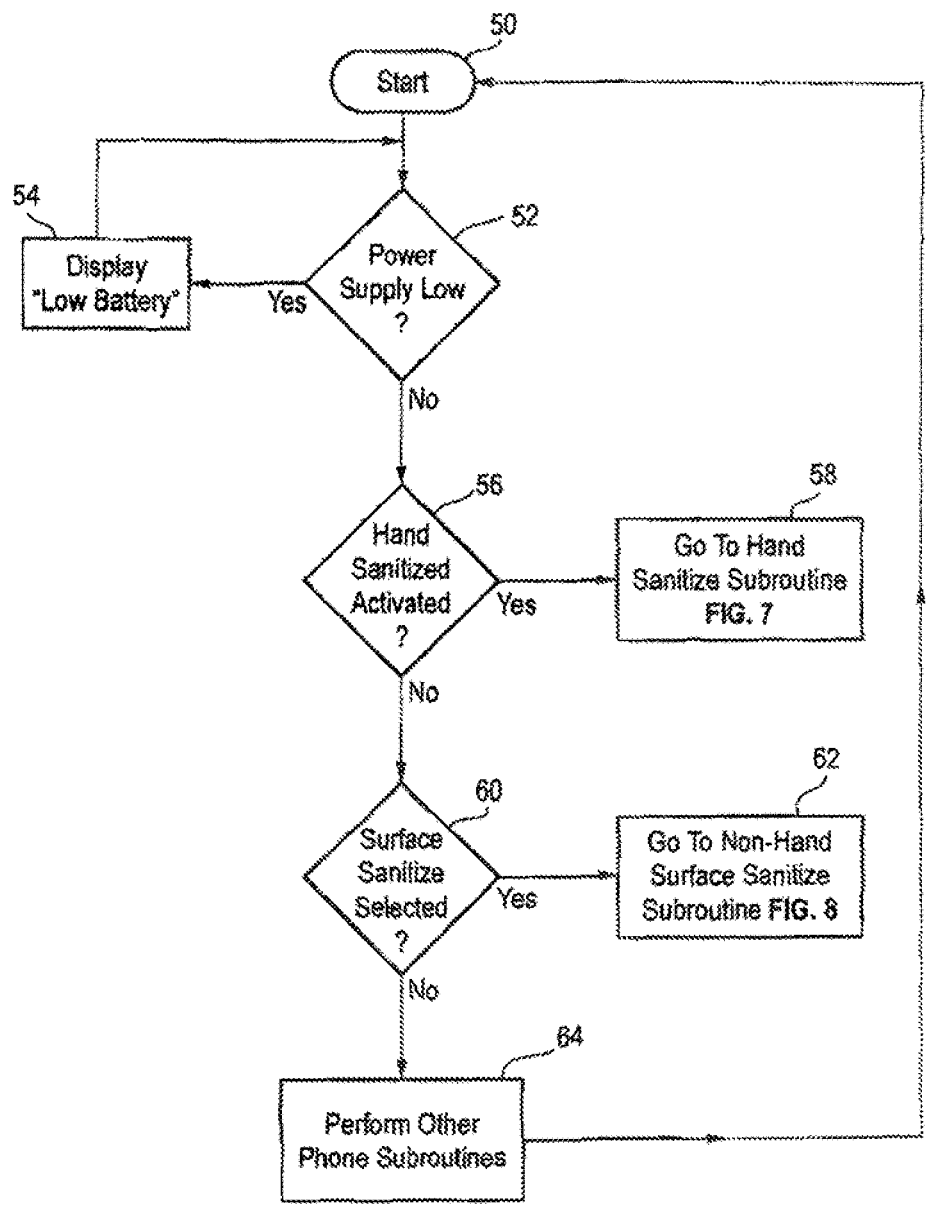
FIG. 6 is a logic flow chart of the operation of the sanitizing cellular telephone of FIGS. 1-5.
Figure 7:
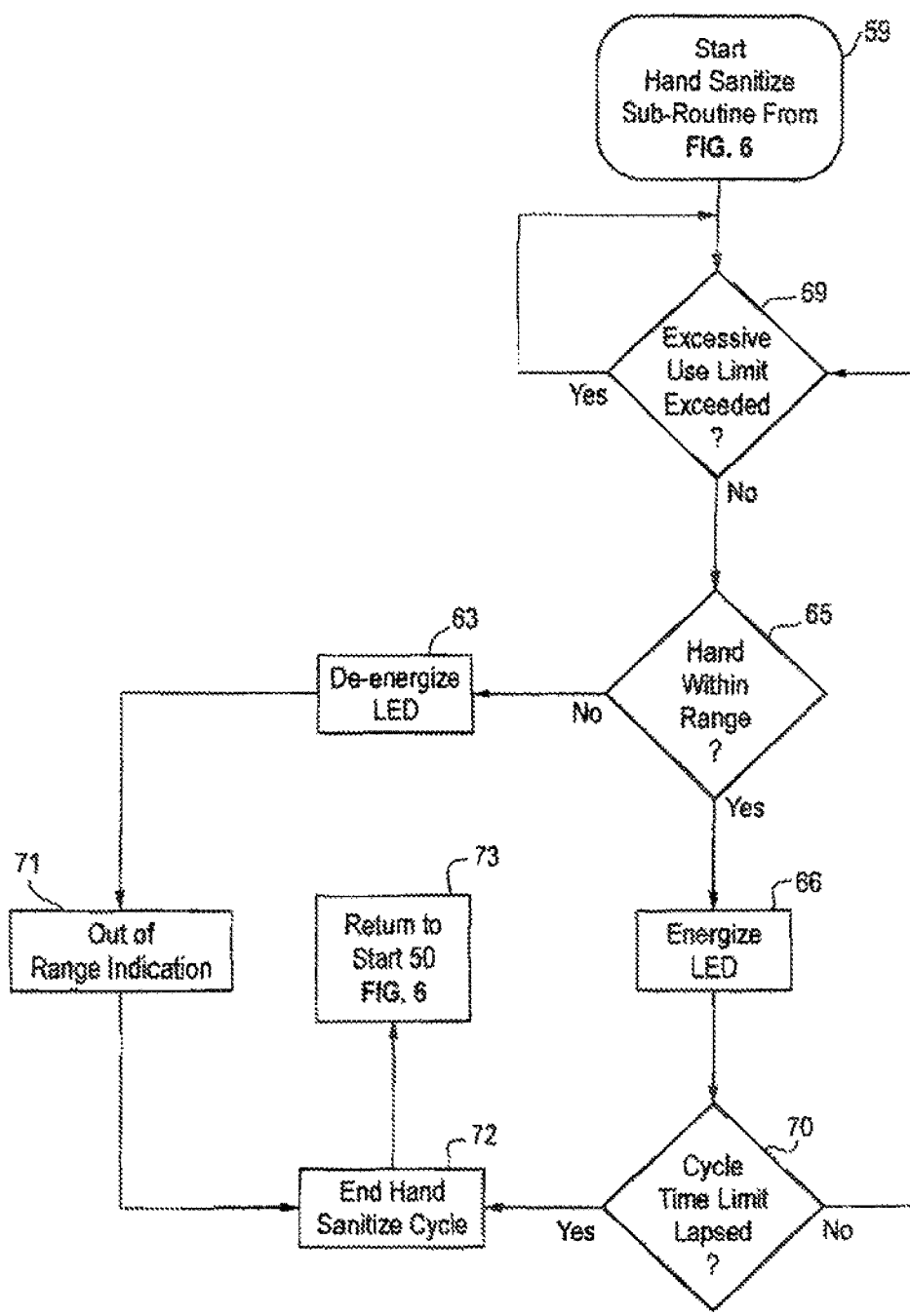
FIG. 7 is a logic flow chart of a sub-routine of FIG. 6 relating to performance of the hand sanitizing function.
Figure 8:
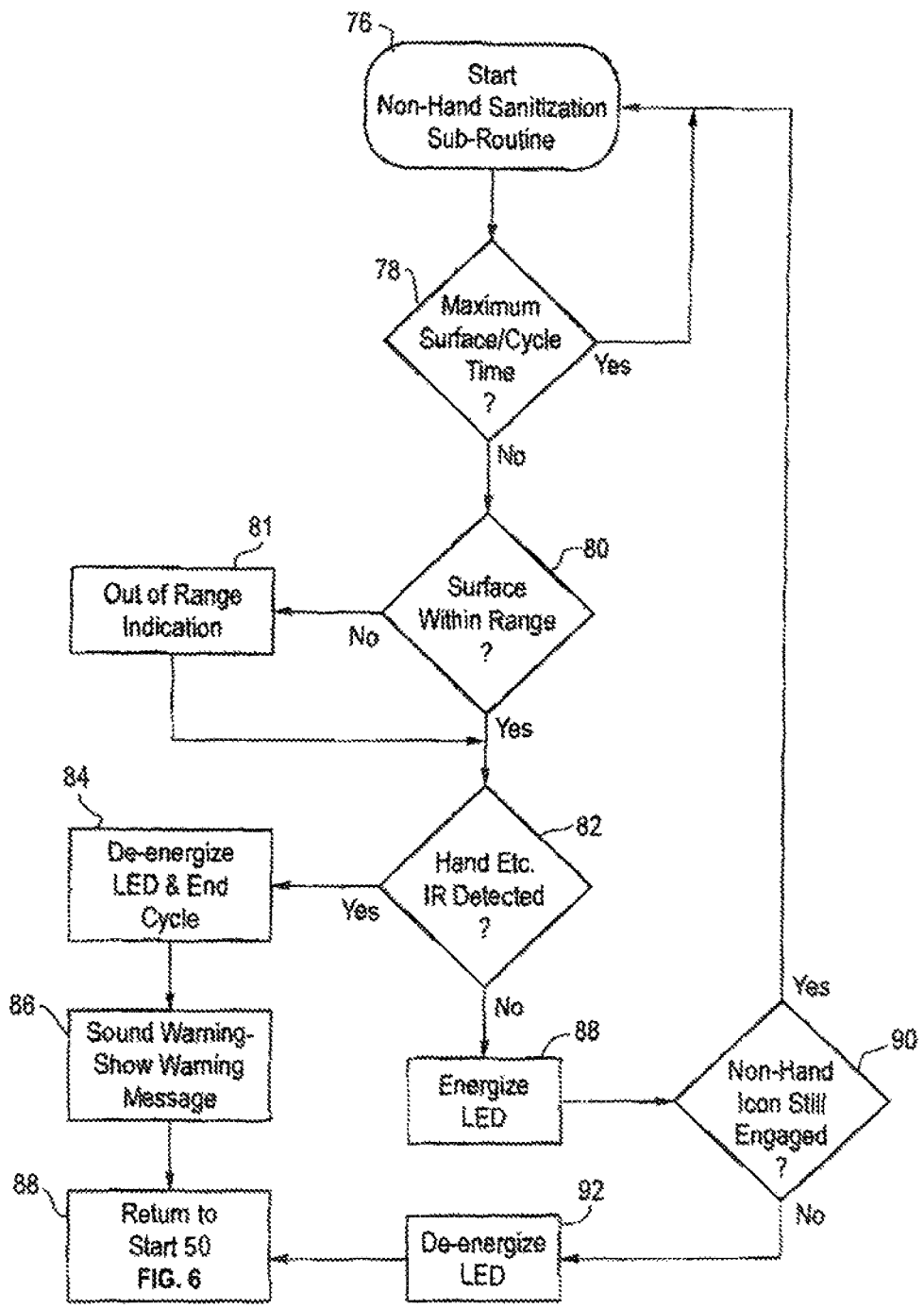
FIG. 8 is a logic flow chart of a sub-routine of FIG. 6 relating to performance of the non-hand, surface sanitizing function.

The controller 16, FIG. 1A contains a microprocessor with appropriate software to perform all the normal functions of a cellphone needed to be performed in whatever way they are normally performed, while the novel sanitizing functions of the present invention are performed in accordance with the logic flow charts of FIGS. 6-8.

Referring now to the logic flow chart of FIG. 6, relating to the operation of the hand and surface sanitization functions of the sanitizing cell phone 10, after program start 50, a determination is made in step 52 as to whether the battery power is too low to continue normal telephone functions and sanitization functions. If so, then in step 54, an indication of the battery 20 being too low for operation is provided on the screen until the battery 20 is recharged.

If the power supply is adequately charged, then in step 56, a determination is made as to whether the user has touched the hand sanitizer icon 44, FIGS. 2 and 4, to initiate a hand sanitization cycle. If so, then in step 58, the program moves to the hand-sanitize subroutine program of FIG. 7. If not, then in step 60 the hand sanitization cycle has been activated by the user, then in step 60, a determination is made as to whether the surface sanitization icon 46, FIGS. 2 and 5, has been touched to begin a non-hand surface sanitization cycle. If so, then in step 62, the program moves to the surface sanitizing subroutine program of FIG. 8. If not, the program moves to step 64 and selected performance of all the routine and normal operations of a cellular telephone, such as those noted above. The program returns to start 50 and recycles, as described above.

Referring to FIG. 7, after the start 59 of the hand sanitize subroutine, in step 69 a determination is made as to whether the accumulated rolling time use has been exceeded, suggestive of excessive use during a given one or two-hour period, for example. If it has not been exceeded, the program proceeds to step 65, and if it has been exceeded, then after some time without use, the limit will no longer be exceeded and the program can again move to step 65.

In step 65, a determination is made as to whether the target hand is within proper range for safety and effective sanitization. If so, then the program moves to step 66 where the LED is energized. If not, then the hand sanitize cycle never begins, and if it has begun, it is terminated. the LED 12 is deenergized in step 63, an out of range indication, audible or message or both is given in step 71. Next, the hand sanitize cycle is ended in step 72, the program returns to the start 50 of the main program in step 73

After the LED 12 is turned on in step 66, in step 70, a determination is made as to whether the preselected hand sanitize cycle time limit has lapsed.

Alternatively, once the hand is detected to be out of range, the LED is deenergized and the hand sanitization cycle ends and is not restarted until the hand sanitization icon 44 is retouched is also done if any one of the periods that the LED has been deenergized for longer than a preselected maximum time during which the viruses would be able to recover before the next period of radiation. It is expected that after a number of cycles of operation, the user will learn to keep their hand at the correct distance for sanitization and the range finder will not often be used.

If the maximum sanitize cycle time limit has not been exceeded, the program returns to start 60, and the above steps continue to be cycled through until the maximum time limit has been reached. Once the maximum cycle time has lapsed, then in step 72, the hand sanitize cycle is ended and the LED 12 turned off. The program then returns to start 50, FIG. 6.

Referring now to FIG. 8, after start 76 of the non-hand, surface sanitizing subroutine, a determination is made in step 78 as to whether a preselected excessive surface sanitization time limit has been exceeded. If so, the program waits until sufficient time has passed such that the time limit is no longer exceeded. If not, then the program moves to step 80, where it is determined whether the suspect surface is within sanitization range so that the radiation intensity at the suspect surface is strong enough to kill viruses, etc. If not, then in step 81, an out of range indication, either audibly or visually on the touch screen 18.

Once the target surface is within the appropriate distance range from the LED, in step 82, it is determined whether a hand is being detected by the IR sensor 38, indicating that the user is using the phone to sanitize their hand without the safety features of the hand sanitize cycle, described above, or worse, whether the user has turned the light toward their own face and eyes. If so, then the LED will not be energized even if the non-hand surface sanitization icon is being pressed. Instead, in step 84, the LED 12, if already energized, will be deenergized and the non-hand surface sanitization cycle will be ended. Next in step 86, a sound warning is sounded and a warning message is provided advising what has happened and why and cautioning the user not to do so again.

This feature will prevent a user from causing excessive radiation of a person's hand which is otherwise prevented during the hand sanitization subroutine 62, FIGS. 6 and 8, by limiting the on time to a predetermined maximum time period. This feature, of course, also protects a person's eyes and face from possibly damaging UV light radiation.

If no hand or other warm body is detected in step 82, then in step 88 the LED 12 is energized. Next, in step 90, a determination is made as to whether the non-hand surface sanitization icon 46, FIG. 5, is still being engaged by the user's finger. If so, and so long as the icon 46 is engaged no longer than the maximum cycle time, the LED 12 will remain energized. If not, then in step 92, the surface sanitization cycle is ended with the de-energization of the LED.

A relatively unlimited cycle time for non-hand surface sanitization is permitted due to the fact, that unlike hand sanitization there is not risk of injury, and surface sanitization may require greater amounts of radiation to ensure that all surface viruses, etc. have been disabled or killed users can rely upon their own judgment.

Figure 9:
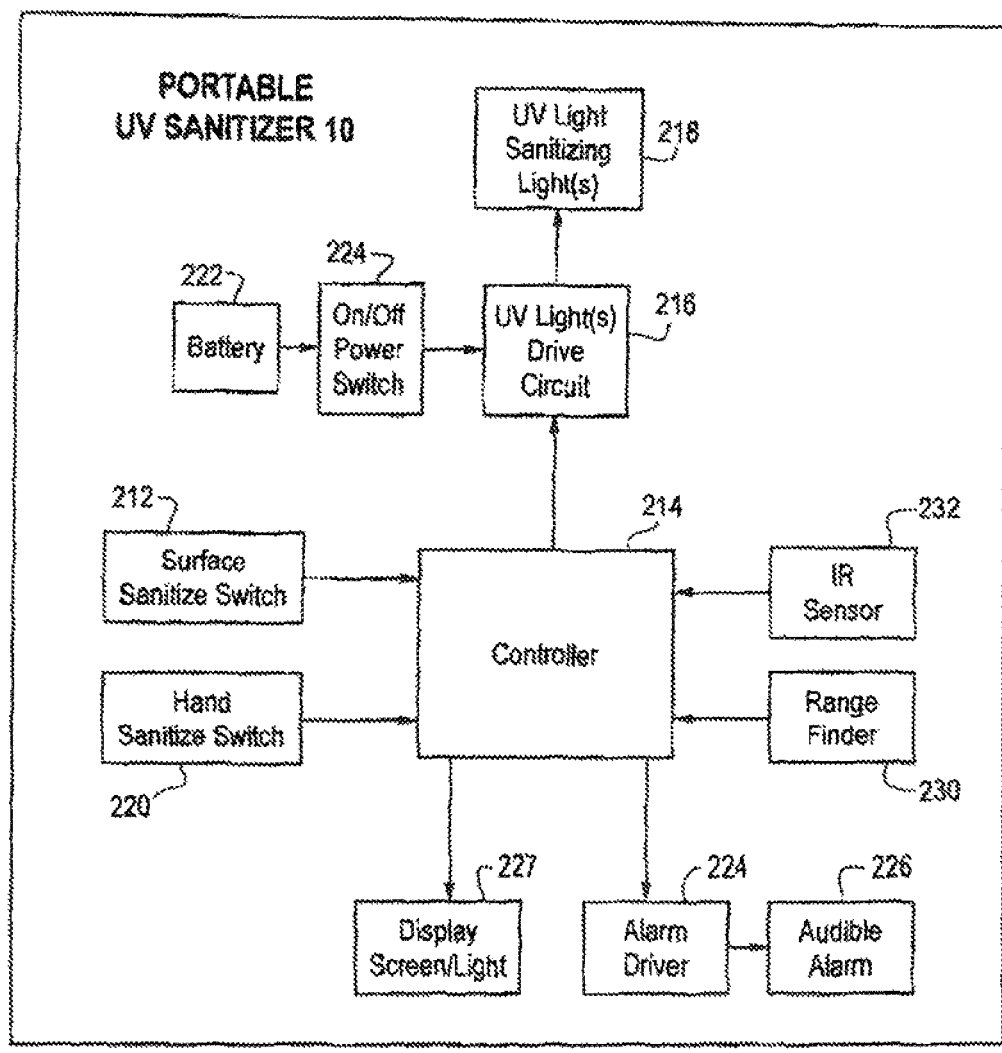
FIG. 9 is a functional block diagram of a preferred embodiment of the safe, portable UV hand and surface sanitizer that does not also incorporate features of a cellphone.
Figure 10:
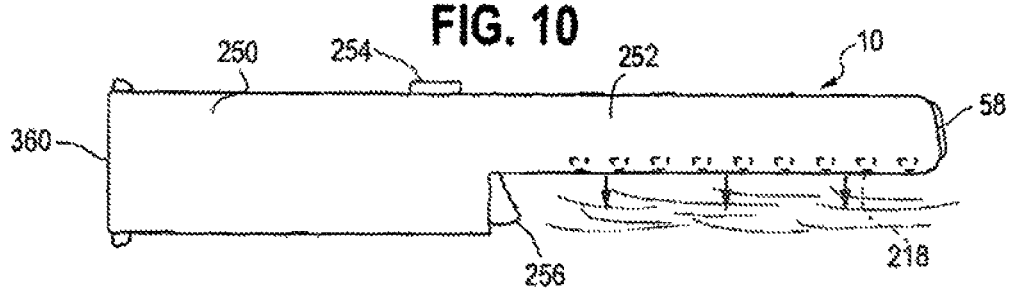
FIG. 10 is a side elevation view of one embodiment of the safe UV hand sanitizer of FIG. 9 with the configuration of an elongate light wand.
Figure 11:
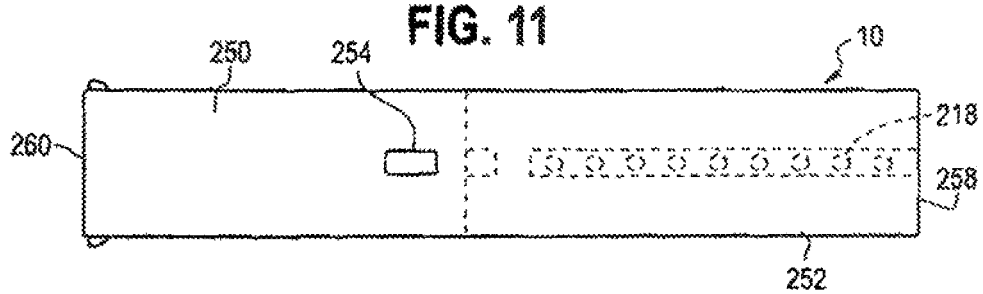
FIG. 11 is a top, or plan, view of the UV light sanitizer of FIG. 10.

Referring to FIG. 9, shown is a functional block diagram of other configurations of the sanitizer of the present invention that are not associated with or function with a cellphone. This enables acquisition of the benefits of the UV light sanitizer without having to incur the higher cost of a cellphone sanitizer 10. These other configurations are still approximately no larger than a cellphone and are easy to carry and handle. These other configurations include the fixed light wand configuration of FIGS. 10-13, the flash light configurations of FIGS. 14-16 and of FIGS. 17-13 and the foldable light wand configuration shown in FIGS. 20-22.

All four non-cellphone configurations have the functional block diagram of FIG. 9 and operate in accordance with the logic flow charts of FIGS. 23, 24 and 25, described below.

As with the cellphone embodiment of FIG. 1A, there are two different modes of operation. If a surface sanitize switch 212 is actuated, then a microprocessor controller 214 causes a UV lights drive circuit 216 to energize UV light sanitizing lights 218 pursuant a surface sanitize control program described in detail below with reference to FIGS. 23 and 25. If a hand sanitize switch 220 is actuated, then the controller 214 causes the UV lights drive circuit 216 to energize the UV sanitizing light 218 pursuant to a hand sanitize control program described in detail below with reference to FIGS. 23 and 25.

Pursuant to the hand sanitize program, so long as the non-skin surface sanitize mode is actuated with switch 212, the UV light source 18 will remain energized unless an IR detector 32 detects a user's hand, face or other skin of a user or other person or a maximum time limit has lapsed. When the IR detector 232 senses an infrared target, the controller 214 also causes an alarm driver 224 to sound an audible alarm 226 to provide a warning alert so the user knows why the UV lights 18 were automatically turned off. This automatic turn-off feature advantageously prevents the user from excessively radiating the hand when in the hand sanitize mode or inadvertently radiating their own face or the skin of a third person when in the surface sanitization mode.

The rechargeable battery 222 provides all the power for the sanitizer 210 when an on/off switch 224 is actuated to a power-on state. A suitable USB or other battery recharging port (not shown) is provided to recharge the battery 222.

There is no risk of injury from excessive radiation of an inanimate surface. However, the automatic turn-off feature may be provided to reduce the risk of inadvertent depletion of a rechargeable battery 222. However, when the hand sanitize switch 220 is actuated and the controller enters into the hand sanitize mode, other precautions are taken to prevent injury to the user from excessive use. Once the switch 220 is initially actuated, the controller causes the driver 216 to energize the UV light 218 but only for a preselected safe time period. Once the preselected safe time period has lapsed, such as two to ten seconds depending upon UV radiation intensity, the UV light 218 is automatically deenergized regardless of whether the regardless of whether the hand sanitize switch is held in an actuated state, if not a momentary contact switch, or if the switch 220 is held actuated or repetitively activated during the preselected time maximum hand sanitization cycle period.

In addition to the single cycle turnoff feature, another feature of the invention that prevents excessive radiation prevents the user from initiating too many hand-sanitization cycles during one or more given past predetermine time periods, such as one to a few hours or twenty-four hours, by ignoring actuations of the hand sanitize switch until enough time has passed to insure against excessive UV radiation.

In addition, another feature of the embodiment of FIG. 1A is protection of the user from injury due to locating the UV lights 218 too close to the user's hand. The intensity at a hand or other surface being radiated depends upon a combination of the intensity at the UV source and the distance from the UV light source and the target surface being radiated. If the target is so close to the person's hand when in the hand sanitize mode, this is detected by a range finder 230 which causes the controller 214 to deenergize the UV lights 218 and end the hand sanitization cycle. In addition, the controller 214 will the audible alarm 226 to provide an indication of why the cycle was ended.

If the UV light source 218 is too far removed from the target hand, then the time allotted to radiation in the hand sanitize mode may be too short to actually kill all of the pathogens. If the range finder 230 detects that the target hand is too far away for the UV light source to be effective to kill all the virus during the preselected hand sanitization cycle period, then the hand cycle period is automatically ended and an audible alarm or audible message is provided to indicate to the user what has happened and why.

Likewise, if the UV light source 218 is too far away from the target surface the time period of radiation may become excessive or may become ineffective regardless of the length of time that the surface is radiated. Accordingly, in the preferred embodiment, the controller will cause the alarm 26 to sound whenever the target surface is too2 far away to be effectively radiated.

One aspect the invention is the method of training a user the proper distance range for effective and safe use through the use of use of the different out of range audible alarms.

Although, other UV light frequencies could be used to sanitize surfaces, preferably the UV light operates to produce UV-C light waves, wavelength 200-280 nm., which are believed to be optimum for killing or otherwise disabling corona viruses, such a COVID-19, other viruses, infectious bacteria, and other possibly dangerous infectious microorganisms. The UV light source may comprise a plurality of UV LEDs, as shown in the cellphone embodiment of FIG. 1.

As noted, the length of time that a pathogen must be radiated with the UV light to be disabled depends upon the intensity of the UV light where it impinges the target surface. Both the optimum radiation time and intensity needs to be determined empirically or from available results of UV light sanitization scientific studies and may vary for different infectious microorganism. Within a median range, the greater the intensity the shorter the time needed to sanitize and vice versa. As a matter of convenience of use, the maximum time duration should be less than ten seconds. The UV light radiates outwardly in all directions from the back of the cell phone until it impinges a surface.

In order for an entire hand to be radiated it must be located a minimum distance from the cell phone. If the hand is too close, then the light will impinge only a part of the hand with full intensity which may be potentially damaging in addition to being ineffective to sanitize any part of the hand which is not being radiated. Also, if the hand is too far away from the UV light source 218 the UV light may be too spread out and thus too weakened to kill or disable pathogens on the hand. An adjustable or nonadjustable lens may be provided to focus or defocus the light being admitted by the LED light source 218.

Accordingly, in accordance with one aspect of the invention, means are provided to assist the user to locate their hand at an optimum distance from the source of the UV radiation and to thereby prevent failure to sanitize or damage to a user's hands due to concentrated UV radiation on the only one part of a user's hand. Preferably, the distance range is approximately six to ten inches, but this distance should be determined empirically once the initial radiation intensity of the LED is determined. Also, some UV LED's are more efficient than others and thus the light energy may vary even if the input energy remains the same.

As noted, the intensity of the radiation on a hand or surface, in addition to depending upon the intensity of the light as it leaves the UV light source 218, also depends upon the distance between the 218 and the surface being radiated. The farther the UV light source is from the hand or suspect surface, the weaker will be the intensity of the radiation on the surface, and vice versa. If target distance is too close, then the intensity may be too great and cause possible injury to a hand. If the target distance is too great, then the intensity may be insufficient to kill the viruses, etc.

The controller 214 preferably responds to signals from the range finder 230 to control the UV light source 218, increasing or decreasing drive or turning the LED off if too close to a person's hand or providing distance information to the user via the speaker, such as an audible warning message, such as "Too close!", or by displaying on the touch screen a message or other visual indication of range status. While there is no danger in locating the light to close to a non-skin 2target surface, preferably, the range finder 40 is also used when the cellular phone 10 is being used to sanitize a non-skin target surface to make sure that the surface is not too far away for effective sanitization.

The use of range finders in cameras have been used for many years, but the preferred type of range finder is one that is coupled to the focus mechanism so that the lens is focused correctly when the rangefinder duplicate images. The range finders currently being used in cellular phones with a camera having a variable focal range or zoom feature. The range finder 230 has two spaced ports (not shown) for receipt of light that face in the same direction in which the UV light source 218 is directed.

If the UV light 18 is not one or more UV LEDs, then the drive circuit will need to be compatible. Drive circuits for other UV lights, such a fluorescent, incandescent, quartz, etc. are well known, but UV LED's are preferred due to their small size, modest power requirement and low operating temperature.

Alternatively, the drive circuit 16 can provide a drive signal of varying input power in response to signals from the controller 216 by varying the resistance of the current limiting resistor 233 to increase or decrease the intensity based on the distance from the target as determined by the range finder 230. However, should the hand be still be detected too far out of range even at maximum intensity, then the LED may be automatically be turned off, and the user will have to start a new cycle to sanitize their hand.

Figure 12:
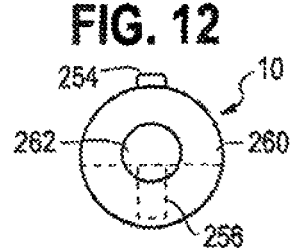
FIG. 12 is an elevational view of a back end of the safe UV sanitizer of FIGS. 10 and 11.
Figure 13:
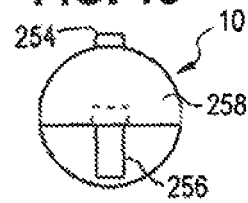
FIG. 13 is an elevation view of a front end of the safe UV hand sanitizer of FIGS. 10, 11 and 12.

Referring first to FIGS. 10-13, in one configuration, an elongate wand 252 with a series of UV LEDs are mounted along the length of the wand 252 which is mounted to a handle 250 which houses the battery, controller and other components shown in FIG. 9. A spring-loaded slide switch 254, which functions as the non-hand surface sanitization activation switch 212 of FIG. 9, is mounted on top of the handle 250, and a trigger-like switch 256 performing the function of the hand sanitizing actuation switch 220 of FIG. 9 mounted to the forward end of the handle 250 and widely spaced from the switch 254 to avoid any confusion between the two. Referring to FIG. 12, a power on-off switch 262 performing the function of the on-off switch 224 of FIG. 9 is mounted at a back end 260 of the handle opposite the front end 258 of the wand 252.

Figure 14:
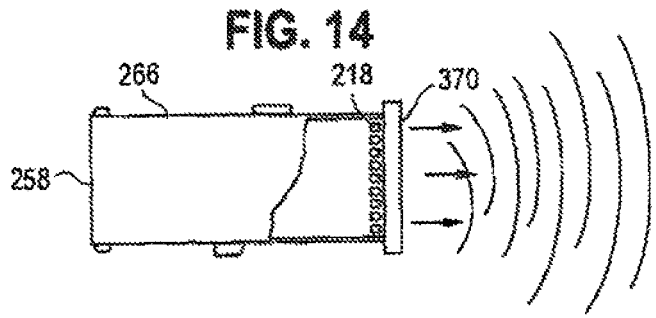
FIG. 14 is a side elevational view of another form of the sanitizer of FIG. 25 with a body having a cylindrical, flashlight configuration with the UV light radiation being emitted from a front end.
Figure 15:
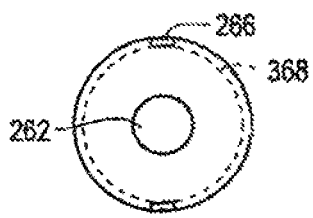
FIG. 15 is an elevation view of a back end of the safe UV sanitizer of FIG. 14.
Figure 16:
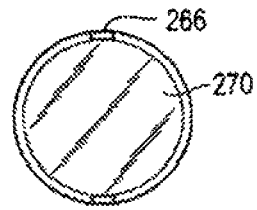
FIG. 16 is a side elevational view of a front, light emitting end of the safe UV hand sanitizer of FIG. 14.

A flashlight configuration of the portable, safe UV hand sanitizer is shown in FIGS. 14-16 in which a tubular housing 266 with a transparent lens 270 at one end in front of one or more UV lights 218 to shine UV light axially outwardly from the lens to either a user's hand or a non-skin. A pushbutton, power on-off switch 262 is mounted to one end 266 of the housing opposite to the one end with the lens 270 and UV lights 218.

A third configuration of the safe UV hand sanitizer 10, is shown in FIGS. 17-19 which is similar to that of FIGS. 14-16, except that the lens and light is pointed in a direction that is transverse to the axial direction of the tubular body 250.

A fourth configuration of the portable, safe UV hand sanitizer 10 is shown in FIGS. 20-22, which is similar to the configuration shown in FIGS. 10-13 except that the forward section 252 carrying the UV lights is pivotally connected to the housing 250 by a pivot axle 274.

The method of use of the present invention includes the concept of training a user to locate their hand at the correct distance from the camera for optimum results by virtue of a number of initial failed attempts in which the LED is automatically turned off due to the hand being out of range.

In addition to the time for a single cycle of hand sanitization being automatically limited, preferably the controller 14 stores and keeps a running total of the number of hand cycles performed in a past preselected time period, such as two hours, and automatically prevents performance of another hand sanitization cycle if the number of hand sanitization cycles exceeds a preselected maximum number during the preselected time period indicating excessive use deemed to be possibly unsafe. A running total is kept, so that after a period of time has passed without any sanitization cycles have been run, a new hand sanitization may again be initiated. In such case, an audio message or visual message or other visual indication on the touch screen 18 why a new hand sanitization cycle cannot be initiated and advising of when sufficient time has passed to resume use of the hand sanitization function. Again, the method of the present invention contemplates that successive denials of operation of the hand sanitization cycle due to excessive cycles during a given preselected period will result a teaching or conditioning a user not the perform to excessive cycles over to short of a time to be safe.

Figure 23:
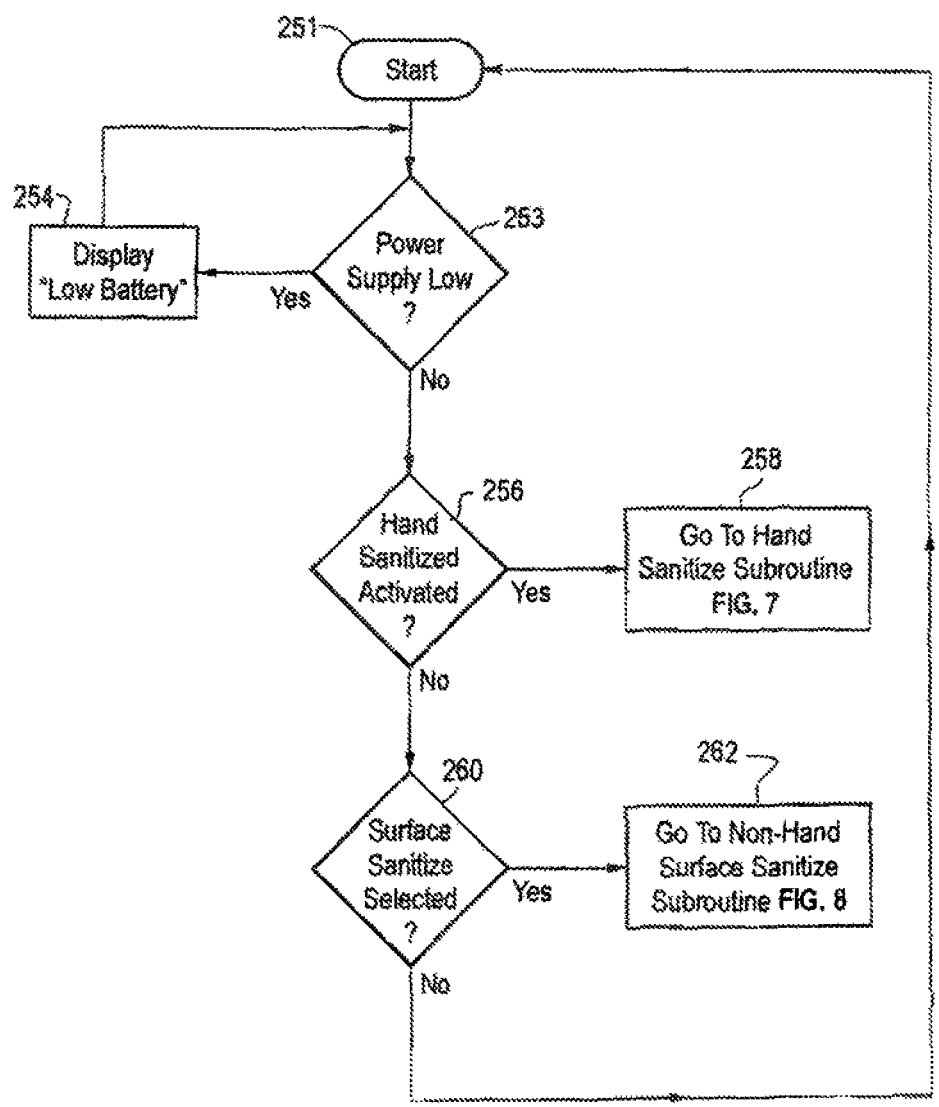
FIG. 23 is a logic flow chart of the operation of the sanitizer.

Referring now to the logic flow chart of FIG. 23, shown is the logic flow chart for the software operating program loaded in the microprocessor controller for operation of the sanitizers of FIGS. 10-22. After program start 251, a determination is made in step 253 as to whether the battery power is too low to continue normal telephone functions and sanitization functions. If so, then in step 25f, an indication of the battery 224 being too low for operation is provided on the screen until the battery 224 is recharged.

If the power supply is adequately charged, then in step 256, a determination is made as to whether the user has actuated the hand sanitize switch 220 to initiate a hand sanitization cycle. If so, then in step 258, the program moves to the hand-sanitize subroutine program of FIG. 24. If not, then in step 260 the hand sanitization cycle has been activated by the user, then in step 260, a determination is made as to whether the surface sanitization switch 246, has been touched to begin a non-hand surface sanitization cycle. If so, then in step 262, the program moves to the surface sanitizing subroutine program of FIG. 25. If not, the program moves to step 264 and selected performance of all the routine and normal operations of a cellular telephone, such as those noted above. The program returns to start 50 and recycles, as described above.

Figure 24:
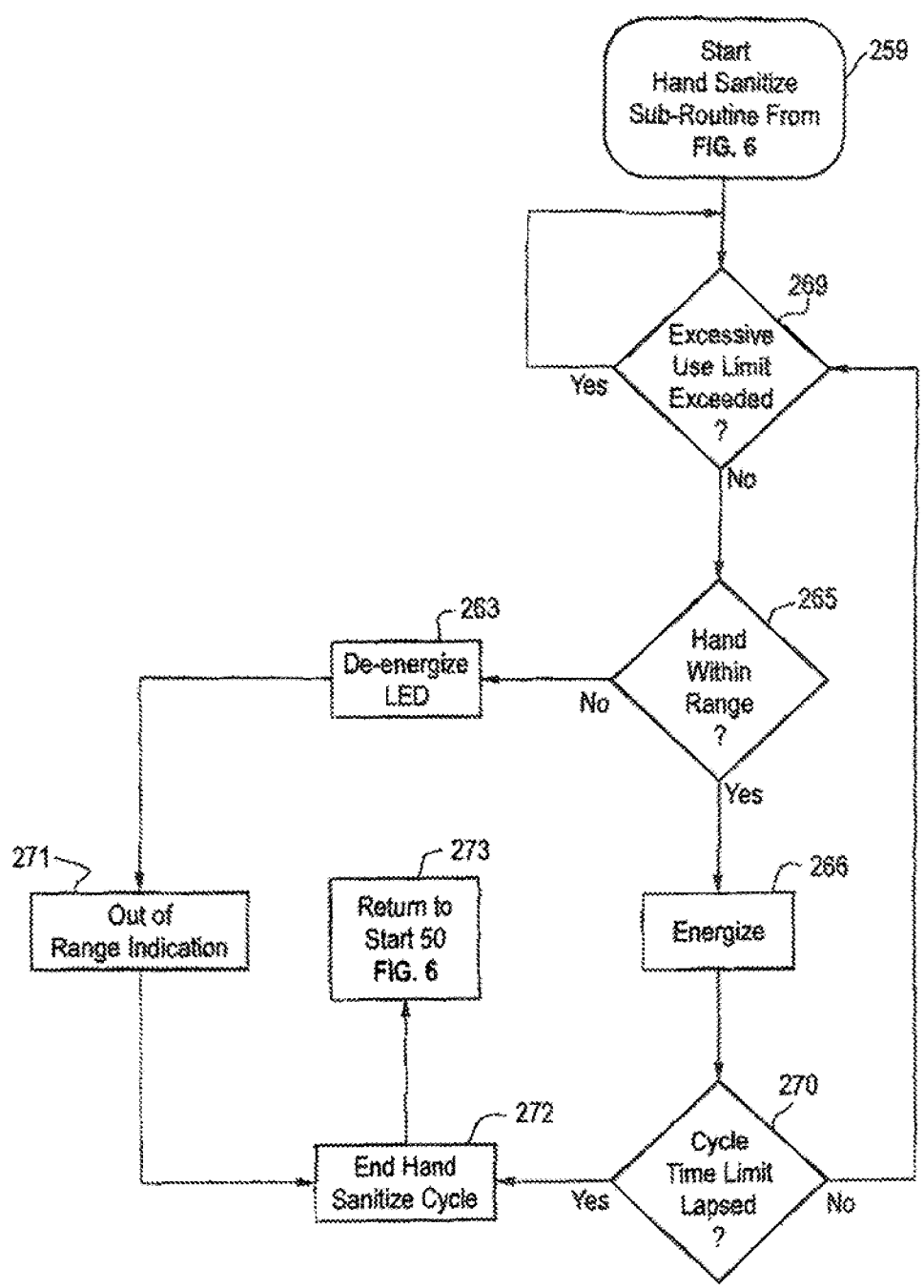
FIG. 24 is a logic flow chart of a sub-routine of the program of FIG. 23 relating to performance of the hand sanitizing function.

Referring to FIG. 24, after the start 259 of the hand sanitize subroutine, in step 269 a determination is made as to whether the accumulated rolling time usage has been exceeded, suggestive of excessive use during a given one or two-hour period, for example. If it has not been exceeded, the program proceeds to step 265, and if it has been exceeded, then after some time without use, the limit will no longer be exceeded and the program can again move to step 265.

In step 265, a determination is made as to whether the target hand is within proper range for safety and effective sanitization. If so, then the program moves to step 66 where the LED is energized. If not, then the hand sanitize cycle never begins, and if it has begun, it is terminated. the LED 218 is deenergized in step 263, an out of range indication, audible or message or both is given in step 271. Next, the hand sanitize cycle is ended in step 272, the program returns to the start 250 of the main program in step 273

After the LED 218 is turned on in step 266, in step 270, a determination is made as to whether the preselected hand sanitize cycle time limit has lapsed. Alternatively, once the hand is detected to be out of range, the LED is deenergized and the hand sanitization cycle ends and is not restarted until the hand sanitization switch is re-actuated if any one of the periods that the LED has been deenergized for longer than a preselected maximum time during which the viruses would be able to recover before the next period of radiation. It is expected that after a number of cycles of operation, the user will learn to keep their hand at the correct distance for sanitization and the range finder will not often be used.

If the maximum sanitize cycle time limit has not been exceeded, the program returns to start 260, and the above steps continue to be cycled through until the maximum time limit has been reached. Once the maximum cycle time has lapsed, then in step 272, the hand sanitize cycle is ended and the UV light 18 is turned off. The program then returns to start 250, FIG. 23.

Figure 25:
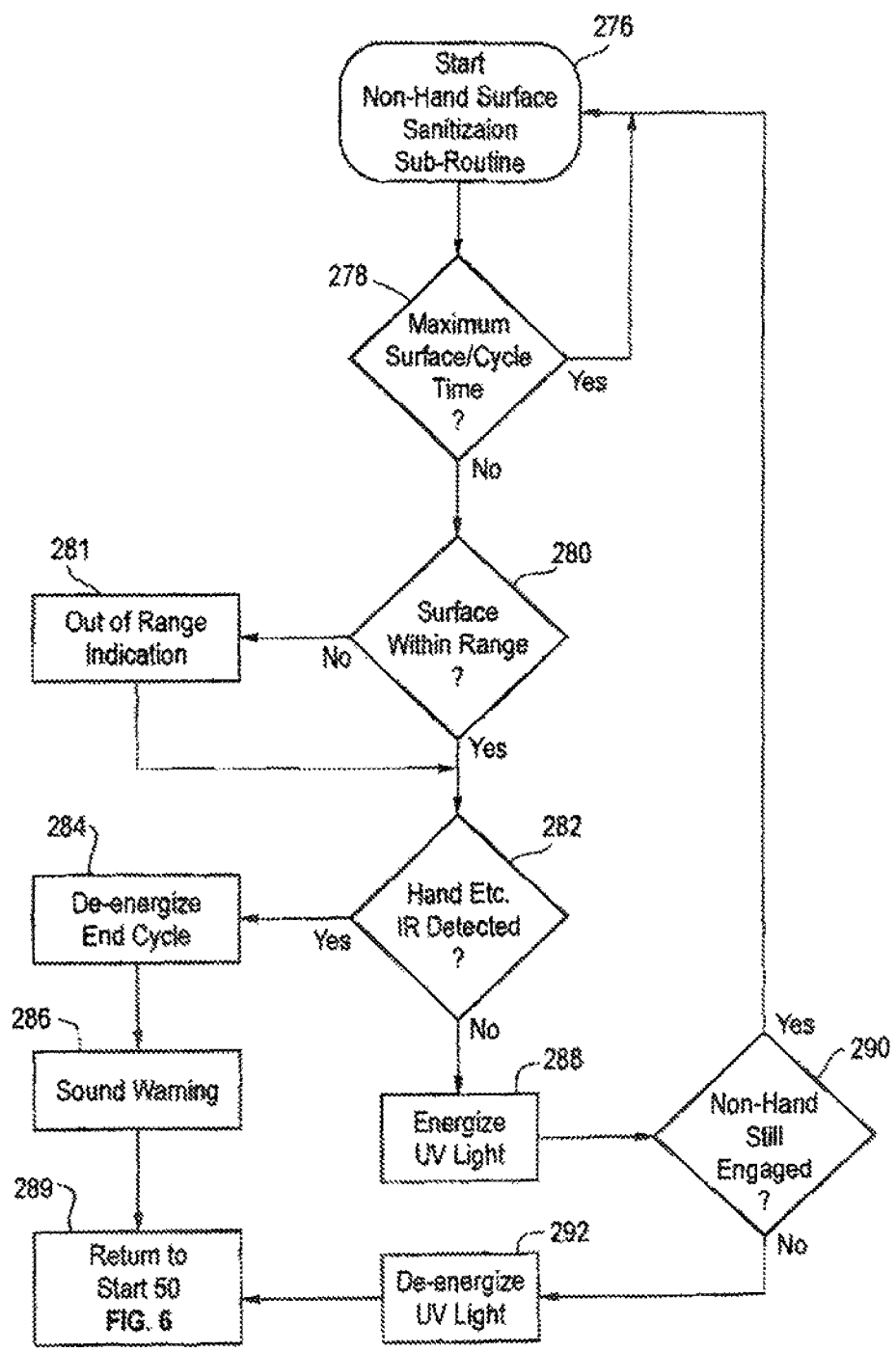
FIG. 25 is a logic flow chart of a sub-routine of FIG. 23 relating to performance of the non-hand, surface sanitizing function.

Referring now to FIG. 25, after start 276 of the non-hand, surface sanitizing subroutine, a determination is made in step 278 as to whether a preselected excessive surface sanitization time limit has been exceeded. If so, the program waits until sufficient time has passed such that the time limit is no longer exceeded. If not, then the program moves to step 280, where it is determined whether the suspect surface is within sanitization range so that the radiation intensity at the suspect surface is strong enough to kill viruses, etc. If not, then in step 281, an out of range indication, either audibly or visually on the touch screen 218.

Once the target surface is within the appropriate distance range from the LED, in step 282, it is determined whether a hand is being detected by the IR detector 232, indicating that the user is using the phone to sanitize their hand without the safety features of the hand sanitize cycle, described above, or worse, whether the user has turned the light toward their own face and eyes. If so, then the LED 218 will not be energized even if the non-hand surface sanitization icon is being pressed. Instead, in step 284, the LED 228, if already energized, will be deenergized and the non-hand surface sanitization cycle will be ended. Next in step 86, a sound warning is sounded and a warning message is provided advising what has happened and why and cautioning the user not to do so again.

This feature will prevent a user from causing excessive radiation of a person's hand which is otherwise prevented during the hand sanitization subroutine 262, FIGS. 23 and 25, by limiting the on time to a predetermined maximum time period. This feature, of course, also protects a person's eyes and face from possibly damaging UV light radiation.

If no hand or other warm body is detected in step 82, then in step 289 the LED 12 is energized. Next, in step 90, a determination is made as to whether the non-hand surface sanitization switch 212, FIG. 9, is still being engaged by the user's finger. If so, and so long as the icon 246 is engaged no longer than the maximum cycle time, the LED 18 will remain energized. If not, then in step 292, the surface sanitization cycle is ended with the de-energization of the LED 218.

A relatively unlimited cycle time for non-hand surface sanitization is permitted due to the fact, that unlike hand sanitization there is not risk of injury, and surface sanitization may require greater amounts of radiation to ensure that all surface viruses, etc. have been disabled or killed. Users can rely upon their own judgment.

Referring to FIGS. 26, 27 and 28, the UV sanitizer 10 may also be configured as part of a cell phone protector configuration 310 of the UV hand sanitizer of the present invention is shown protectively attached to a cellphone 312. The cellphone 311 has the usual elements including a touch screen 314, a power on-off switch 3316, volume control switches 18, a screen view on-off switch 320, a speaker 322, a charging/data port 324 and a camera lens with a built-in flash 325. The touch screen 312 displays a plurality of application icons 326 associated with the usual telephone communication and other functions.

The UV hand sanitizer 310 has a rigid housing 313 surrounded by flexible, resilient attachment arms 315 with inward hook-like fingers 317 that resiliently attach the housing 313 to the back of the cellphone. If there is a camera33 lens 25 at the back of the cellphone, then the top 19 of the housing is located beneath the camera lens 325 and a camera light passageway 327 is provided extending through the upper resilient attachment arm.

A charging/data connection port 321 at the bottom of the sanitizer is connectable to the charging/data port 324 to either, or both, of a battery charger and the charging/data port 324 of the cellphone 11. Preferably, the UV hand sanitizer 10 has its own rechargeable battery connected to the charging/data port 321. Alternatively, the hand sanitizer 10 receives power from the rechargeable battery of the cellphone 311 through a suitable connector (not shown), but then the cellphone battery may become depleted through use of the hand sanitizer 10.

The actuation and control signals associated with the icons 326 and 328 may be passed to the hand sanitizer 310 via a connection through such a connector between the ports 3321 and 24. Alternatively, the sanitizer 10 has an antenna to receive control signals from the cellphone 311 in response to actuation of either of icons 3326 and 28.

In general, the UV hand sanitizer 310 of FIGS. 1-3 may be constructed substantially the same as the surface sanitizer shown in U.S. Pat. No. 10,265,540 issued to Yehezkel on Apr. 23, 2019, for "Mobile Device Case with Ultraviolet Light Sanitizer and Light Therapy", hereby incorporated by reference, except it lacks the therapeutic light features of that device and includes the novel features of the present invention that enable safe radiation of a user's hand, prevent inadvertent radiation of a user's face and insures that radiation of surfaces is of sufficient intensity to be effective in killing surface pathogens.

In accordance with the preferred embodiment of the present invention, a software program, UV Hand Sanitization App, described in detail below with reference to FIGS. 36-38 is loaded into the microprocessor controller of the cellphone 311, and after this occurs, two UV sanitization icons, as shown in greater detail in FIGS. 4 and 5, are presented for use on the touch screen to control UV sanitization. Icon 326 shown in greater detail in FIG. 9A, when touched by the user, initiates a program for safe UV sanitization of a user's hand by the UV hand sanitizer 10 with one or more UV LEDs, 311. Icon 44, FIG. 4, when touched by the user, initiates a program for safe UV sanitization of a user's hand by the UV hand sanitizer 10.

As in the prior configurations, in the cellphone protector configuration Unlike known portable, non-hand UV sanitizers noted above, which provide no effective means for preventing a person from use on a user's hand or face that could be harmful, in accordance with the present invention, such means are provided. The UV sanitizer 10 of current invention prevents either mistakenly intentional, or inadvertent, excessive use on a person's skin, even a non-user's skin. Both modes of operation associated with the hand sanitize icon of FIG. 4 and the surface sanitize icon of FIG. 5, have such safety features that reduce the risk of damage to a person due to excessive exposure to UV light.

Figure 33:
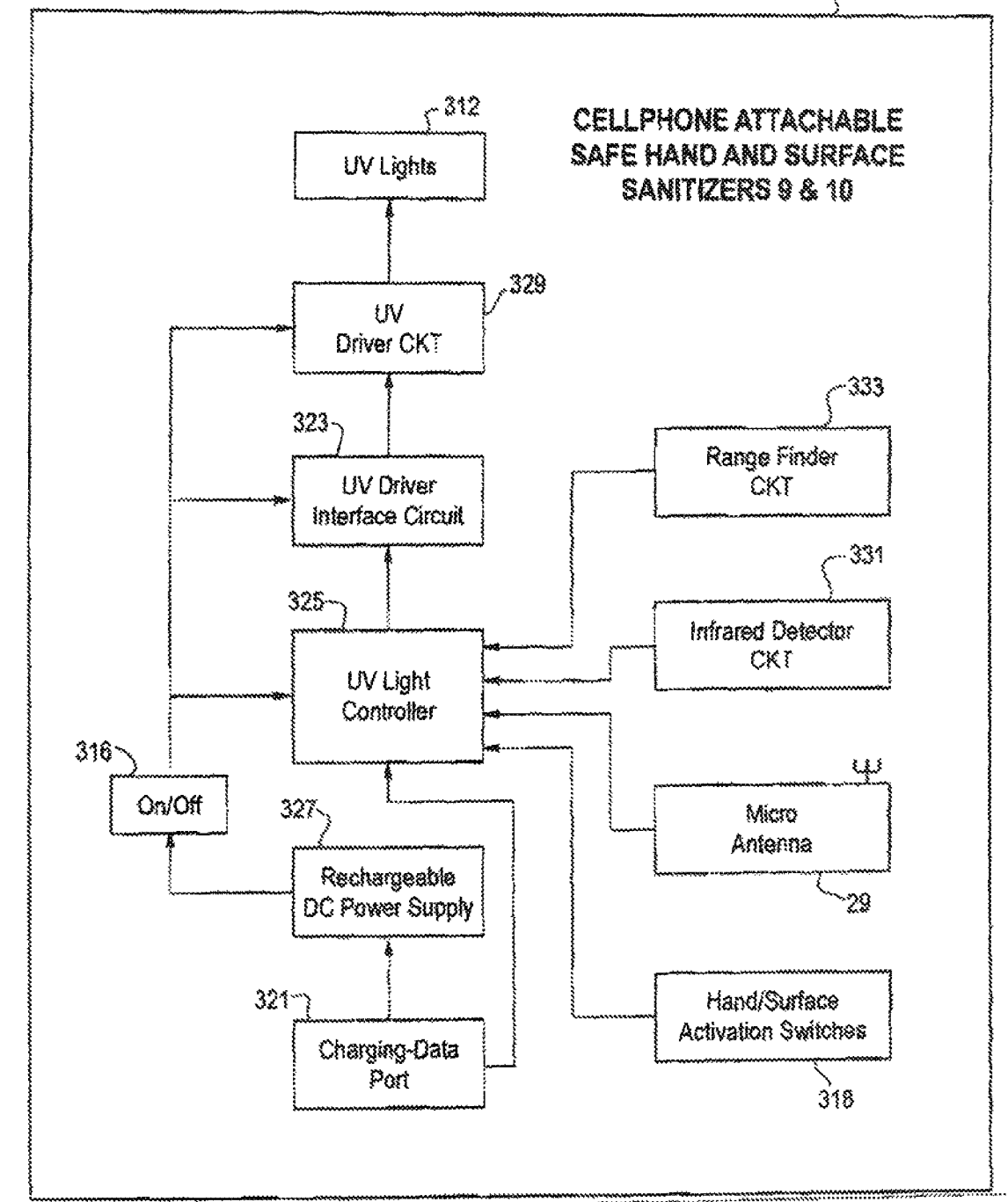
FIG. 33 is a functional block diagram of the major components of the UV sanitizers of FIGS. 28-30 and 31-33.
Figure 34:
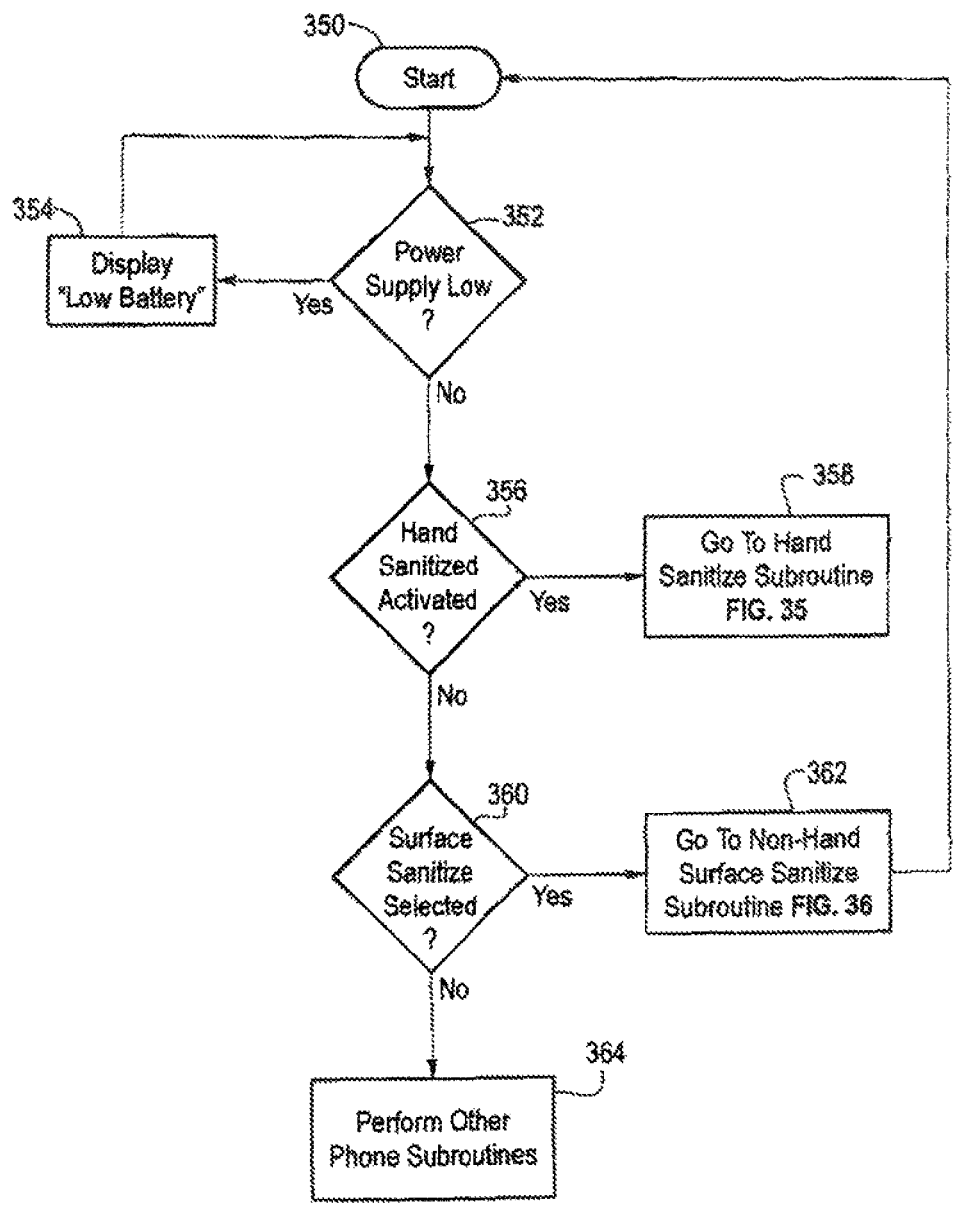

As explained in greater detail with reference to FIGS. 312-314, for this purpose, an infrared sensor 330 is provided to sense when a person's skin is detected during operation in the surface sanitization mode to immediately terminate UV radiation. The controller 325 shown in FIG. 33 is also programmed to automatically terminate radiation after a preselected time after initiation of operation in the hand sanitization mode. Moreover, the controller disables use if there are too many initiations of the hand sanitization mode during a preselected period which has been determined to be excessive and potentially injurious.

As noted earlier, another shortcoming of known UV surface sanitizers is that there is nothing to ensure that the sanitization radiation is of sufficient intensity to kill or disable pathogens on a suspected surface because the UV light source is too far away from the suspect surface to be effective. This problem is addressed in accordance with the present invention by means including provision of a range finder 332 with spaced light receivers 333 and 335 means responsive to the range finder 332 to control radiation or control information to a user to find the correct maximum distance from the target surface to ensure that the radiation on a selected surface is effective.

FIGS. 29, 30 and 31 show another UV sanitizer 9 which has all of the features of the embodiment of FIGS. 26-28 except that it does not perform a cellphone protection function and has a male charging/data connector 334 for releasable connection to the female charging/data port 324 of the cellphone 311. When the male charging/data port 334 is connected to the female charging/data port 324, the UV hand sanitizer 10 of FIGS. 29-31 becomes releasably but firmly attached to the cellphone 311, and the cellphone 311 then may be used as a handle to hold the sanitizer 10 during sanitization operations. In addition, when there is a connection, the rechargeable battery of the cellphone 11 may be used to power the UV hand sanitizer 10. If the sanitizer 10 is provided with its own rechargeable battery, then the connection may be used to recharge the sanitizer battery from a conventional battery recharger or from the cellphone.

The connection of the ports 324 and 334 also enables communication between the cellular telephone 311 when the icons 326 or 328 are touched. Alternatively, the sanitizer 10 is provided with an internal radio antenna for receipt of control signals from the cellphone.

If the sanitizer 10 is provided with its own battery, then two control switches 334 and 336 may be provided to control the hand sanitize and surface sanitize functions in lieu of the icons 326 and 328. In such case, the sanitizer 9 may be used without any connection to the cellphone 311.

Referring to FIG. 32, the sanitizer 10 may be provided with an extension cord 338 to enable movement of the sanitizer 10 independently of the cellphone 311. The extension cord having a female connector 340, like the female connector of the port 324, for connection with the male connector 334, and a male connector 342 for connection with the female connector of the/data port 24 of the cellphone 311.

As seen in the functional block diagram of FIG. 8, in addition to the features already shown and described above with reference to FIGS. 26-32, the UV sanitizers 10 has a UV light controller 325, a UV driver interface circuit 323, a UV driver circuit 329, a range finder circuit 337 for operating the range finder 333 and interfacing with the controller 325, an infrared detector circuit 331 for operating the infrared detector 30 and interfacing it with the controller 325 and a micro-antenna circuit for interfacing the cellphone 311 with the UV light controller 325 if communication is not accomplished through the mating of the charging/data ports 324 and 321.

UV hand sanitizers of FIGS. 26-33, of the present invention, unlike known cellular telephones, has an ultraviolet lamp, or UV LED 312, that under control of the user, may be safely used to UV sanitize a user's hand in addition to being usable to sanitize a suspicious non-hand surface, or surface, such as a door handle, food item, etc. As previously noted, although, other UV light frequencies could be used to sanitize surfaces, preferably the UV LED operates to produce UV-C light waves, wavelength 200-280 nm., which are believed to be optimum for killing or otherwise disabling corona viruses, such a COVID-19, other viruses, infectious bacteria, and other possibly dangerous infectious microorganisms.

The length of time that a pathogen must be radiated with the UV light to be disabled depends upon the intensity of the UV light where it impinges the target surface. Both the optimum radiation time and intensity needs to be determined empirically or from available results of UV light sanitization scientific studies and may vary for different infectious microorganism. Within a median range, the greater the intensity the shorter the time needed to sanitize and vice versa. As a matter of convenience of use, the maximum time duration should be less than ten seconds. The UV light radiates outwardly in all directions from the back of the cell phone until it impinges a surface.

In order for an entire hand to be radiated it must be located a minimum distance from the cell phone. If the hand is too close, then the light will impinge only a part of the hand with full intensity which may be potentially damaging in addition to being ineffective to sanitize any part of the hand which is not being radiated. On the other hand, no pun intended, if the hand is too far away from the light the light may be too spread out and thus too weakened to kill or disable pathogens on the hand. An adjustable or nonadjustable lens may be provided to focus or defocus the light being admitted by the LED.

Accordingly, in accordance with one aspect of the invention, the range finder 332 is automatically used to assist the user to locate their hand at an optimum distance from the source of the UV radiation and to thereby prevent failure to sanitize or do damage to a user's hands due to concentrated UV radiation on the only one part of a user's hand. The range finder 332 is also used when sanitizing a surface to make sure that the surface is not so distant that the intensity of radiation on the surface is insufficient to effectively kill or disable pathogens on the surface.

Preferably, the distance to the target is approximately six to ten inches, but this distance should be determined empirically once the initial radiation intensity of the LED is determined. Also, some UV LED's are more efficient than others and thus the light energy may vary even if the input energy remains the same. Accordingly, the intensity of the radiation on a hand or surface, in addition to depending upon the intensity of the light as it leaves the UV LED 312, also depends upon the distance between the LED 312 and the surface being radiated. The farther the LED 312 is from the hand or suspect surface, the weaker will be the intensity of the radiation on the surface, and vice versa. If target distance is too close, then the intensity may be too great and cause possible injury to a hand. If the target distance is too great, then the intensity may be insufficient to kill the viruses, etc.

While the method of use of the present invention includes the step of providing operating directions to the user with respect to the optimum, maximum and minimum distances, in accordance with the present invention, the range finder 332 is provided to determine the distance to which the sanitizer may be from the target when the LED is being actuated. The controller 325 responds to signals from the range finder 332 to control the LED, increasing or decreasing drive or turning the LED off if too close to a person's hand or providing distance information to the user via the speaker 322 of the cellphone 11, such as an audible warning message, such as "Too close!", or by displaying on the touch screen 12 a message or other visual indication of range status.

While there is no danger in locating the light to close to the target surface, preferably, the range finder 340 is also used when the cellular phone 311 is being used to sanitize a non-hand surface to make sure that the surface is not too far away for effective sanitization. The use of range finders in cameras have been used for many years, but the preferred type of range finder is one that is coupled to the focus mechanism so that the lens id focused correctly when the rangefinder duplicate images. The range finder may be just like those found in modern cameras having a variable focal range or zoom feature or in autofocus binoculars or single purpose telescopic range finder. IR sensing cameras are shown in U.S. patent application 2019/0364227 filed November, 2019 by McManus et l., which is hereby incorporated by reference, and many other IR detector related devices may easily be found in the patent art.

In addition, when in the non-hand surface sanitizing mode, the infrared, or IR, sensor 331 receiving infrared light will indicate the presence of the user's face. When this occurs, the controller 325 responds by immediately turn off the UV LED 312 to prevent damage to the user's eyes or facial skin.

The LED drive circuit 329 is controlled by the controller 325 to energize the UV light 12. When actuated, The LED drive circuit 329, may provide an electrical drive signal that yields a fixed level of input power to the LED 312. This occurs whenever the controller 3325 or 328 detects that one of the icons 36 or 38 has been touched, or one of the switches 334 or 336 of the sanitizer 10, has been actuated. When this occurs, the controller turns on a semiconductor switch 348 to connect DC power to energize the LED 312 to generate the desired level of UV light radiation. The voltage of the battery 320 may be approximately 5 VDC.

Alternatively, the drive circuit 314 can provide a drive signal of varying input power in response to signals from the controller 316 to increase or decrease the intensity based on the distance from the target as determined by the range finder 340 to maintain a preselected radiation intensity on the target surface despite changes in distance.

Any number of known drive circuits may be suitable for providing power to the LED 312, such as shown in one or more of U.S. Pat. No. 10,433,381 issued Oct. 1, 2019 to Sakai et al. and 10,582,577 issued Mar. 3, 2020 to Zhao et al. and US. Patent applications 20202019/0053848 filed Oct. 22, 2019, by Lai et al. and 2020/0120768 field Jun. 15, 2019 by Lin et al., all of which and the patents cited therein being are hereby incorporated by reference.

When this hand sanitization icon is momentarily pressed or touched by a user of the phone to sanitize the user's hand, then, if the hand is detected by the range finder 340 to be at a suitable distance from the phone 10, the controller causes a hand sanitize cycle to be initiated in which the LED 312 is turned on, but the time that it remains on and the intensity are automatically limited to ensure safety.

Should the hand be detected out of range by the range finder 340, then the LED will be automatically be turned off and the user will have to start a new cycle to sanitize their hand.

The LED could be controlled to automatically turn back on if the user moves their hand back into range, but sanitization depends not only upon the intensity of the radiation but also on the time duration of continuous radiation. A radiation cycle with a fixed total amount of time of radiation that is paused and then is restarted sometime later would possibly allow the pathogens to recover and reduce the effectiveness of such an intermittent hand sanitization cycle. Accordingly, in accordance with the present invention, a restart of the hand sanitization cycle is required once interrupted due to the user's hand being out of range. The restart can then result in a full uninterrupted period of UV radiation. The restart is preferably achieved by the user touching the hand sanitization icon again.

Alternatively, the target distance as sensed by the range finder 333 may be used to vary the intensity of the UV light being radiated by the UV LED 12 to maintain a uniform level of radiation on the target within preselected range limits. When the distance is increased, the radiation from the LED is increased proportionately to maintain the desired intensity on the target, and vice versa.

The method of use of the present invention includes the concept of training a user to locate their hand at the correct distance from the camera for optimum results by virtue of a number of initial failed attempts in which the LED is automatically turned off due to the hand being out of range.

In addition to the time for a single cycle of hand sanitization being automatically limited, preferably the controller stores and keeps a running total of the number of hand cycles performed in a past preselected time period, such as two hours, and automatically prevents performance of another-hand sanitization if the number of hand sanitization cycles exceeds a preselected maximum number during the preselected time period indicating excessive use deemed to be possibly unsafe.

A running total is kept, so that after a period of time has passed without any sanitization cycles have been run, a new hand sanitization may again be initiated. In such case, an audio message or visual message or other visual indication on the touch screen why a new hand sanitization cycle cannot be initiated and advising of when sufficient time has passed to resume use of the hand sanitization function.

Again, the method of the present invention contemplates that successive denials of operation of the hand sanitization cycle due to excessive cycles during a given preselected period will result a teaching or conditioning a user not the perform to excessive cycles over to short of a time to be safe.

Because inanimate surfaces are not going to be injured or damaged by UV light, there is no absolute need to limit the duration of the radiation, and the LED may be kept energized for as long as the user keeps pressing the surface sanitization icon. Preferably, an audio signal may be provided after preselected time period long enough to generally be sure that a surface has been sanitized based on the distance from the suspect target surface, as determined by the range finder 340.

While not needed for purposes of safety, the LED light 312 is preferably turned off automatically after another preselected time period to save battery power in the event the LED is being kept activated inadvertently or grossly excessively.

The controller 325, FIG. 8, contains a microprocessor (not shown) with appropriate software need to perform all the functions of the sanitizer in accordance with the logic flow charts of FIGS. 36, 37 and 38.

Referring now to the logic flow chart of FIG. 36, relating to the operation of the hand and surface sanitization functions of the sanitizers of FIGS. 28-33, after program start 350, a determination is made in step 352 as to whether the battery power is too low to continue normal telephone functions and sanitization functions. If so, then in step 354, an indication of the battery 320 being too low for operation is provided on the screen until the battery 320 is recharged.

If the power supply is adequately charged, then in step 356, a determination is made as to whether the user has touched the hand sanitizer icon 326, FIGS. 1A and 9A, to initiate a hand sanitization cycle. If so, then in step 356, the program moves to the hand-sanitize subroutine program of FIG. 13. If not, then in step 360, a determination is made as to whether the surface sanitization icon, has been touched to begin a non-hand surface sanitization cycle. If so, then in step 362, the program moves to the surface sanitizing subroutine program of FIG. 33. If not, the program moves to step 364 and selected performance of all the routine and normal operations of a cellular telephone, such as those noted above. The program returns to start 350 and recycles, as described above.

Referring to FIG. 38, after the start 359 of the hand sanitize subroutine, in step 369 a determination is made as to whether the accumulated rolling time use has been exceeded, suggestive of excessive use during a given one or two-hour period, for example. If it has not been exceeded, the program proceeds to step 365, and if it has been exceeded, then after some time without use, the limit will no longer be exceeded and the program can again move to step 365.

In step 365, a determination is made as to whether the target hand is within proper range for safety and effective sanitization. If so, then the program moves to step 66 where the LED is energized. If not, then the hand sanitize cycle never begins, and if it has begun, it is terminated. the LED 312 is deenergized in step 363, an out of range indication, audible or message or both is given in step 371. Next, the hand sanitize cycle is ended in step 372, the program returns to the start 350 of the main program in step 373.

After the LED 312 is turned on in step 366, in step 370, a determination is made as to whether the preselected hand sanitize cycle time limit has lapsed.

Alternatively, once the hand is detected to be out of range, the LED is deenergized and the hand sanitization cycle ends and is not restarted until the hand sanitization icon 44 is retouched is also done if any one of the periods that the LED has been deenergized for longer than a preselected maximum time during which the viruses would be able to recover before the next period of radiation. It is expected that after a number of cycles of operation, the user will learn to keep their hand at the correct distance for sanitization and the range finder will not often be used.

If the maximum sanitize cycle time limit has not be exceeded, the program returns to start 360, and the above steps continue to be cycled through until the maximum time limit has been reached. Once the maximum cycle time has lapsed, then in step 372, the hand sanitize cycle is ended and the LED 3312 turned off. The program then returns to start 350, FIG. 36.

Figure 35:
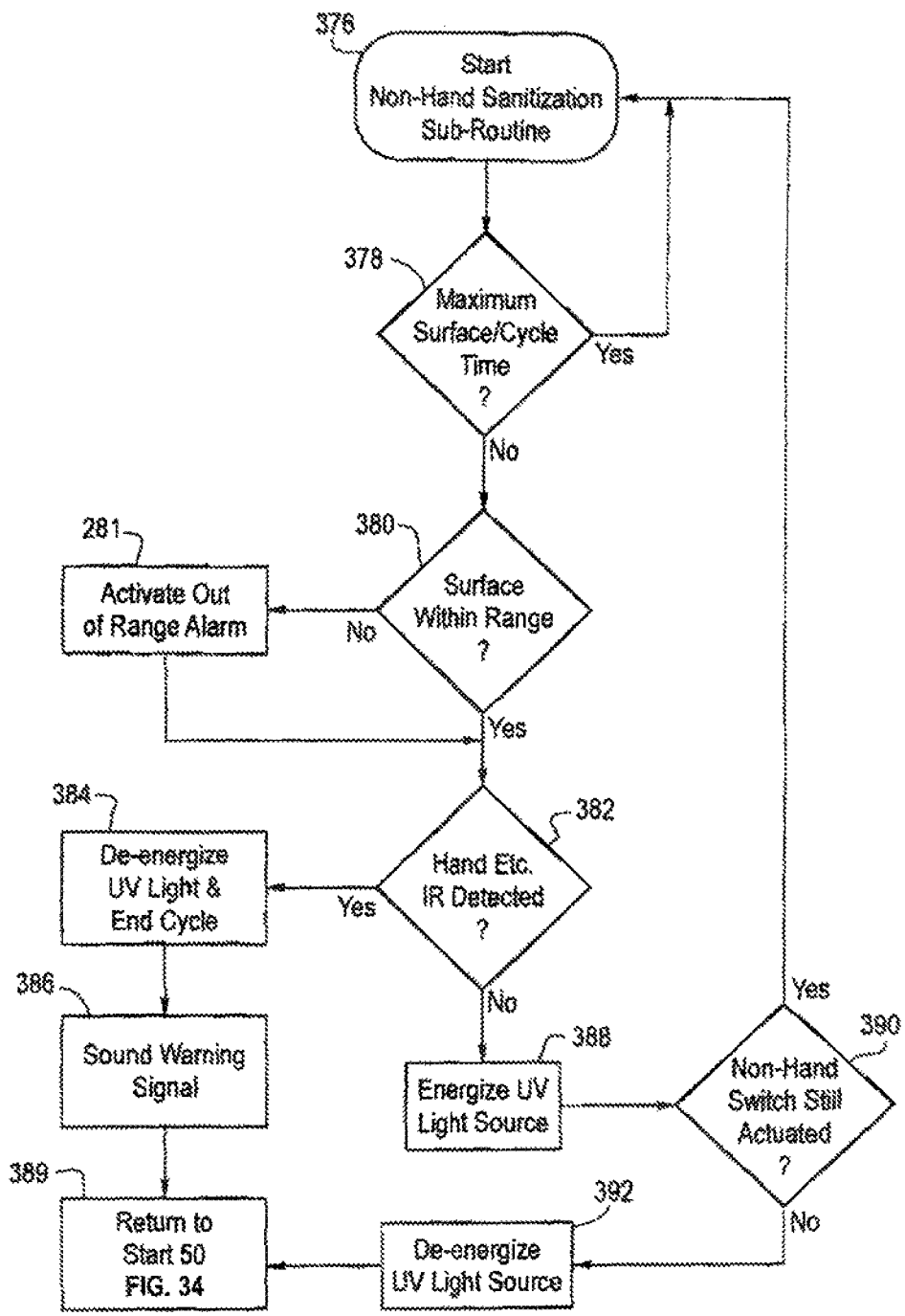

Referring now to FIG. 35, after start 376 of the non-hand, surface sanitizing subroutine, a determination is made in step 378 as to whether a preselected excessive surface sanitization time limit has been exceeded. If so, the program waits until sufficient time has passed such that the time limit is no longer exceeded. If not, then the program moves to step 380, where it is determined whether the suspect surface is within sanitization range so that the radiation intensity at the suspect surface is strong enough to kill viruses, etc. If not, then in step 381, an out of range indication, either audibly or visually on the touch screen 318.

Once the target surface is within the appropriate distance range from the LED, in step 382, it is determined whether a hand is being detected by the IR sensor 338, indicating that the user is using the phone to sanitize their hand without the safety features of the hand sanitize cycle, described above, or worse, whether the user has turned the light toward their own face and eyes. If so, then the LED will not be energized even if the non-hand surface sanitization icon is being pressed. Instead, in step 384, the LED 312, if already energized, will be deenergized and the non-hand surface sanitization cycle will be ended. Next in step 386, a sound warning is sounded and a warning message is provided advising what has happened and why and cautioning the user not to do so again.

This feature will prevent a user from causing excessive radiation of a person's hand which is otherwise prevented during the hand sanitization subroutine, FIGS. 35 and 36, by limiting the on time to a predetermined maximum time period. This feature, of course, also protects a person's eyes and face from possibly damaging UV light radiation.

If no hand or other warm body is detected in step 382, then in step 388 the LED 312 is energized. Next, in step 390, a determination is made as to whether the non-hand surface sanitization icon 346, FIG. 38, is still being engaged by the user's finger. If so, and so long as the icon 346 is engaged no longer than the maximum cycle time, the LED 312 will remain energized. If not, then in step 392, the surface sanitization cycle is ended with the de-energization of the LED.

A relatively unlimited cycle time for non-hand surface sanitization is permitted due to the fact, that unlike hand sanitization there is no risk of injury, and surface sanitization may require greater amounts of radiation to ensure that all surface viruses, etc. have been disabled or killed. Users can rely upon their own judgment.

The various configurations of the UV light hand sanitizer of the present invention enable a number of methods of sterilization that are not believed available with known portable UV sanitizers 36 which either lack features needed to protect the user from unsafe elevated levels of skin radiation One such method includes a method for a user to safely use UV light radiation to reduce the risk of infection from pathogenic viruses or bacteria that may be on a suspect surface that a person wishes to touch or has touched. This method is achieved by performance of the steps of (1) carrying a single hand-holdable personal UV sanitizer with a UV light source selectively actuatable by the user in either (a) a non-skin surface sanitization mode with at least one automatic safety feature to prevent inadvertent UV radiation of a person's skin or (b) a skin surface sanitization mode with at least one automatic safety features to reduce the risks of excessive radiation of a user's skin due to excessive radiation time or excessive radiation intensity, (2) prior to touching any non-skin target surfaces suspected of carrying infectious pathogens, actuating the UV light source in the non-skin surface sanitization mode to selectively radiate said suspected non-skin target surfaces with sufficient radiation intensity to kill or disable any pathogens that may be carried on the suspected non-skin target surfaces, and (3) after touching any suspected non-skin surfaces with a user's hand, actuating the UV light source in a skin surface sanitization mode to radiate the user's hand.

Preferably, when in the non-skin surface sanitization mode, the method includes the steps of (1) ascertaining if the UV light radiation is improperly directed at a person's skin radiation and, if so, automatically terminating the radiation. Also, when in the non-skin surface sanitization mode, the method includes the steps (a) sensing the distance to the target surface with a range finder and (c) responding to the range finder indicating the distance to the non-skin target surface to be too far out of range for the radiation intensity to be sufficiently strong at the non-skin target surface to be effective to kill or disable pathogens on the target surface, and (d) providing an out of range warning or automatically terminating UV radiation of the target surface or providing both an out of range warning and automatically terminating UV radiation of the out of range target surface. Preferably, the user responds to the out of range target distance signal as necessary to locate the UV light source sufficiently close to the target surface to ensure that the radiation intensity is sufficient to kill or disable pathogenic viruses or bacteria on the target surface.

The method includes the step of providing the out of range indication as at least one of (a) a visual light signal, (b) an audio signal or (c) a tactile vibration signal. Preferably, the target surface is illuminated with visible light when being radiated with UV light, and the color or intensity of the visible light is changed to indicate the out of range condition.

In accordance with another method of safely sanitizing a non-skin surface with a personal, portable, hand-held UV light sanitizer is achieved by performing the steps of (1) energizing a UV light source to radiate a surface at which the UV light source may be directed, (2) sensing with an infrared light sensor if the UV light source has been directed at a skin surface and (3) automatically deenergizing the UV light source in response to the skin surface sensing means detecting that the UV light source is directed at a skin surface.

Another method of safely sanitizing a user's skin with a personal, portable hand-held UV light sanitizer having a UV light source by performance of at least one of the steps, when in a skin-sanitization mode, of (1) initiating energization of a UV light source while directed at a person's skin to radiate the use skin with UV light radiation, (2) automatically terminating energization of the UV light source after a preselected maximum sanitization cycle time period, (3) automatically preventing energization of the UV light source whenever the total radiation time during a prior preselected prior time period exceeds a preselected, cumulative maximum safe total radiation time period, and (4) preventing energization of the UV light source until a preselected minimum time period has passed since an immediately prior successive skin sanitization cycle has ended, and when a non-skin surface sanitization mode, maintaining energization of the UV light source for as long as a user holds a UV light source switch in an actuated state.

It should be appreciated that the scope of the invention is not limited to the details of the preferred embodiment described above and that not all of the features of the preferred embodiment of the sanitizing cellular telephone described above need be included and the various functions performed may be accomplished by means not identical to those described herein. Reference should be made to the appended claims for a determination of the scope and spirit of the invention.

The invention claimed is:

1. A personal, portable UV light sanitizer for safely sanitizing a skin surface target of a user by automatically preventing excessive unsafe radiation, comprising:
   a sanitizer housing, being of a size carriable by a user to protectively enclose or mount functional elements of the sanitizer, said functional elements including,
   a UV light source for safely radiating the skin surface target at which the UV light source may be directed, with sufficient intensity to kill or otherwise disable any pathogenic viruses or bacteria that may be on the skin surface target, depending on the duration and intensity of the radiation,
   a portable electrical power source for providing electrical power to the UV light source,
   a drive circuit for selectively connecting electrical power from the power source to the UV light source, and
   risk reducing_means for automatically controlling the drive circuit to prevent excessive, unsafe UV light radiation of the user's skin, said risk reducing means including at least one of
   risk reduction means for automatically disconnecting power from the UV light source a preselected maximum safe radiation cycle time period after initiation of a radiation cycle that will prevent excessive radiation of the user's skin,
   risk reduction means to automatically terminate energization of the UV light source after lapse of a preselected maximum safe cycle time period,
   risk reduction means for preventing, during a preselected radiation past accumulation time period, skin radiation time more than a preselected maximum total time of radiation or more than a preselected maximum number of radiation cycles,
   risk reduction means for preventing energization if less than a preselected time period has passed since the end of an immediately prior successive radiation cycle,
   risk reduction means for automatically terminating energization of the UV light source a preselected time after initiation of energization,
   risk reduction for automatically deenergizing the UV light source if the distance from the light source to the target skin is less than a preselected minimum, and
   risk reduction means for providing a signal to the user when distance between the UV light source and the skin surface target is less than a preselected minimum.

2. The personal, portable UV light sanitizer of claim 1 including
   a range finder, and
   a risk reducing means for controlling the drive circuit to vary the intensity of radiation in direct relationship with the distance to the target, power being applied to the UV light source being increased with increased distance to the target and being decreased with decreased distance to the skin surface target to maintain a level of UV light radiation intensity at the target surface needed to effectively sanitize the target surface and to prevent excessive intensity of radiation of the skin surface target.

3. The personal, portable UV light sanitizer of claim 2 in which the range finder is one of
   a sonar range finder,
   a radar range finder, or
   an optical range finder.

4. The personal, portable UV light sanitizer of claim 1 including
   a range finder and
   a distance indicator responsive to the range finder to provide to the user an indication of distance of the skin_surface target_from the UV light source is too far to effectively kill or disable pathogens on the skin surface target or is too near to safely radiate the skin surface target without injury.

5. The personal, portable UV light sanitizer of claim 4 in which the distance indicator is at least one of
   an audible tone that varies in frequency as the distance varies,
   a visible light that varies in color as the distance varies,
   a visual graphic indication of the distance.

6. The personal, portable UV light sanitizer of claim 1 including
   means for sensing when the UV light source is directed at a person's skin, and
   means responsive to the skin sensing means for providing a discernable indication that the UV light source is being directed at a person's skin by providing one or more of
   an audible signal,
   a visual signal, and
   housing vibrational signal.

7. The personal, portable UV light sanitizer of claim 1 including means for sensing when the UV light source is directed at a person's skin, and in which the risk reducing means is responsive to the skin sensing means for instituting at least one preselected safety measure for preventing excessive radiation of a person's skin.

8. The personal, portable UV light sanitizer of claim 7 in which the skin sensing means includes at least one of
a camera carried by the housing directed at whatever target surface the UV light source is directed and means responsive to images from the camera to detect a person's hand or face,
an infrared sensor for detecting infrared radiation from a person's skin,
a range finder, and
means responsive to the range finder indicating a distance to the target surface greater than a preselected maximum skin radiation distance that is too great to be part of a user's body.

9. The personal, portable UV light sanitizer of claim 7 including
means enabling a user to selectively operate the sanitizer in either a skin sanitization mode or a non-skin surface mode, and in which
the risk reducing means is responsive to the sanitizer being operated in the skin sanitization mode to automatically prevent excessive radiation of a person's skin including at least two of
means for_automatically terminating energization of the UV light source after a preselected maximum safe time period after energization is initiated in the skin sanitization mode,
means for_preventing energization of the UV light source earlier than a preselected minimum period since an immediately earlier successive energization in the skin sanitization mode has ended, and
means for_preventing initiation of energization of the UV light source if a number of energizations initiated in the skin sanitization mode has exceeded a preselected safe number during a prior preselected time period.

10. The personal, portable UV light sanitizer of claim 1 in which the risk reducing_means includes
means for measuring the passage of time,
means for storing the total past skin radiation time performed during a prior preselected accumulative radiation time period, and
means for storing a preselected maximum total accumulative radiation time performed during the preselected accumulative radiation time period, and
means responsive to the accumulative radiation time exceeding the maximum total accumulative radiation time for the past preselected time period_to prevent energization of the UV light source until sufficient time has passed.

11. The personal, portable UV light sanitizer of claim 1 including
a visible light source directed at the target to which the UV light source is directed,
means for energizing the visible light source whenever the UV light source is energized to illuminate the target surface with visible light whenever the UV light source is being energized.

12. The personal, portable UV light sanitizer of claim 11 including
an electronic camera contained within the housing, and
means enabling use of the visible light source as a camera flash light to illuminate an object for a photograph being taken by the camera when the UV light source is not being used to radiate the UV target surface.

13. The personal, portable UV light sanitizer of claim 1 including means for sensing if the UV light source is directed at a person's skin, including
a skin sensing means, and in which
the drive circuit includes an automatic switch responsive to the skin sensing means to automatically operate in a skin surface mode when the light source is directed at a person's skin, and
automatically operate in a non-skin mode when the UV light source is not directed at a person's skin.

14. The personal, portable UV light sanitizer of claim 1 in which the drive circuit controlling means includes
means for sensing when the UV light source is directed at a person's skin, and
a range finder,_and in which
the automatically drive circuit controlling means is responsive to the range finder to automatically terminate energization of the UV light source, if the range finder senses a distance less than a preselected minimum safe distance.

15. The personal, portable UV light sanitizer of claim 1 including
means for detecting if the UV light source is directed at a person's skin, and a range finder, and
an energization controlling means including means responsive to the range finder and to the skin detecting means to automatically deenergize the UV light source when skin is detected and the target distance is less than a preselected safe minimum distance.

16. The personal, portable UV light sanitizer of claim 1 in which
the housing has the configuration of an elongate wand with an opaque handle portion and an elongate translucent portion attached to one end of the handle portion, said translucent portion carrying the UV light source, said UV light source being formed from a series of UV light emitting diodes mounted along the translucent portion.

17. The personal, portable UV light sanitizer of claim 16 in which the translucent portion is pivotally mounted to an end of the handle portion.

18. The personal, portable UV light sanitizer of claim 1 in which the housing is elongate with one end that is translucent to enable UV light to radiate outwardly in from the one end of the housing in an elongate direction.

19. The personal, portable UV light sanitizer of claim 1 in which the sanitizer housing has an elongate opaque handle portion and a translucent portion at one end of the elongate handle portion to enable UV light to radiate outwardly from the elongate handle portion in a direction that is transvers to the elongate handle portion.

20. The personal, portable UV light sanitizer of claim 1 in which said risk reducing means includes at least two, at least three, at least four, at least five or all of the risk reduction means.

21. A personal, portable UV light sanitizer, comprising:
a sanitizer housing having surrounding, enclosing walls including a back wall and a front wall and being of a size enabling easy carry by one hand of a user,
a portable electrical power source;
a source of UV light mounted to the housing, for radiating a target surface spaced from the housing at which the UV light source may be directed, with sufficient intensity to kill or otherwise disable any pathogenic viruses or bacteria that may be on the target surface, if and when the target surface is within a maximum effective distance range of the UV light source;

a drive circuit for connecting the portable power source to the UV light source;

means for sensing at least one characteristic of the target surface at which the UV light source is directed;

a user control switch;

a microprocessor controller powered by the portable power source for controlling the drive circuit to selectively energize the UV light source with the power source in response to the user control switch, or in automatic response to the at least one characteristic of the target sensed by the target characteristic sensing means, said at least one characteristic of the target being the distance from the UV light source to the target, and including means for variably focusing the UV light source in a beam having a beam width at the target surface which may be selectively varied, and means responsive to the focusing means for automatically increasing energization of the UV power source to increase the level of radiation in direct relationship with the width of the beam to maintain a preselected minimum level of radiation intensity at the target surface.

22. A personal, portable UV light sanitizer for sanitizing both non-skin surfaces and skin surfaces, comprising:

a sanitizer housing having surrounding, enclosing walls including a back wall and a front wall and being of a size enabling easy carry by one hand of a user, a portable, rechargeable electrical power source;

a source of UV light mounted to the housing, for radiating a target surface spaced from the housing at which it may be directed, with sufficient intensity to kill or otherwise disable any pathogenic viruses or bacteria that may be on the target surface, if and when the target surface is within a maximum effective distance range of the UV light source;

a drive circuit for connecting the portable power source to the UV light source;

means for sensing whether the target surface at which the UV light source is directed is the surface of a persons' skin or a non-skin surface;

an automatic energization controlling means including a microprocessor controller powered by the portable power source for controlling the drive circuit differently in response to the sensing means depending upon whether the target is sensed to be a skin surface or a non-skin surface;

a range finder for automatically determining the distance to the target at which the UV light source is directed, said energization controlling means being responsive to the range finder to automatically control of the UV light source;

means for sensing when the UV light source is directed at a person's skin;

and, in which the automatic energization controlling means is responsive to the skin sensing means and to the range finder to automatically terminate energization of the UV light source, if the range finder senses a distance less than a preselected safe distance, only when the skin sensing means is detecting that the UV light source is directed at a person's skin.

23. The personal, portable UV light sanitizer of claim 22 including means responsive to the skin surface sensing means for automatically terminating power to the UV light source if the target is sensed to be a skin surface when operating in the non-skin surface mode of operation.

24. A personal, portable UV light sanitizer, comprising:

a sanitizer housing having surrounding, enclosing walls and being of a size enabling easy carry by one hand of a user;

a portable, rechargeable electrical power source;

a source of UV light mounted to the housing, for radiating a target surface spaced from the housing at which it may be directed, with sufficient intensity to kill or otherwise disable any pathogenic viruses or bacteria that may be on the target surface, if and when the target surface is within a maximum effective distance from of the UV light source;

a drive circuit for connecting the portable power source to the UV light source;

means for sensing at least one characteristic of the target surface at which the UV light source is directed;

a microprocessor controller powered by the portable power source for controlling the UV light source to selectively energize the UV light source with the power source in response to the user control switch, or in an automatic response to the at least one characteristic of the target sensed by the target characteristic sensing means, said at least one characteristic of the target being the distance from the UV light source to the target, and including means for variably focusing the UV light source in a beam having a beam width at the target surface which may be varied, and means responsive to the range finder to automatically narrowing the beam as the distance to the target surface increases to maintain the minimum effective level radiation at the target surface.

25. A personal, portable UV light sanitizer for safely sanitizing a skin surface target of a user by automatically preventing excessive unsafe radiation, comprising:

a sanitizer housing protectively enclosing or mounting functional elements of the sanitizer, said functional elements including, a UV light source for safely radiating the skin surface target at which the UV light source may be directed, with sufficient intensity to kill or otherwise disable any pathogenic viruses or bacteria that may be on the skin surface target, depending on the duration and intensity of the radiation, a portable electrical power source for providing electrical power to the UV light source, a drive circuit for selectively connecting electrical power from the power source to the UV light source, and risk reducing means for automatically controlling the drive circuit to prevent excessive, unsafe UV light radiation of the user's skin including means for selectively operating in a non-skin surface mode of operation without operation of the unsafe excessive radiation risk reducing means provided when not in the non-skin surface mode, means for sensing whether the UV light source is directed at a skin surface target when operating in the non-skin surface mode of operation, and means responsive to the skin surface sensing means for disconnecting power from the UV light source immediately if skin is sensed when operating in the non-skin surface mode of operation.

26. A personal, portable UV light sanitizer for sanitizing both non-skin surfaces and skin surfaces, comprising:

a sanitizer housing having surrounding, enclosing walls including a back wall and a front wall and being of a size enabling easy carry by one hand of a user;
a portable, rechargeable electrical power source;
a source of UV light mounted to the housing, for radiating a target surface spaced from the housing at which it may be directed, with sufficient intensity to kill or otherwise disable any pathogenic viruses or bacteria that may be on the target surface, if and when the target surface is within a maximum effective distance range of the UV light source;
a drive circuit for connecting the portable power source to the UV light source;
means for sensing whether the target surface at which the UV light source is directed is the surface of a persons' skin or a non-skin surface;
a user control switch;
a risk reducing means including a microprocessor controller powered by the portable power source for controlling the drive circuit differently in response to the sensing means depending upon whether the target is sensed to be a skin surface or a non-skin surface;
a range finder for automatically determining the distance to the target at which the UV light source is directed, said risk reducing means controlling the drive circuit in response to the range finder to automatically control the UV light source; and
said risk reducing means including means responsive to the range finder and to the skin sensing means to automatically deenergize the UV light source when skin is detected and the target distance is less than a preselected safe minimum distance.

27. A personal, portable UV light sanitizer, comprising:
a sanitizer housing having surrounding, enclosing walls including a back wall and a front wall and being of a size enabling easy carry by one hand of a user,
a portable, rechargeable electrical power source;
a source of UV light mounted to the housing, for radiating a target surface spaced from the housing at which it may be directed, with sufficient intensity to kill or otherwise disable any pathogenic viruses or bacteria that may be on the target surface, if and when the target surface is within a maximum effective distance range of the UV light source;
an energization switch for connecting the portable power source to the UV light source;
means for sensing at least one characteristic of the target surface at which the UV light source is directed;
a user control switch;
a microprocessor controller powered by the portable power source for controlling the energization switch to selectively energize the UV light source with the power source
in response to the user control switch, and
in automatic response to the at least one characteristic of the target sensed by the target characteristic sensing means, and
a visible light source directed at the target to which the UV light is directed; said visible light source including lights of two different first and second colors,
said energizing means energizing the visible light source of one of the first one of colors when the sanitizer is operating in a skin sanitization mode and energizing the visible light source of the second one of the colors when the sanitizer is being operated in a non-skin operating mode.

28. The personal, portable UV light sanitizer of claim 27 including means to provide an indication to a user of whether the sanitizer is operating in the skin radiation mode or the non-skin radiation mode.

29. A personal, portable UV light sanitizer, comprising:
a sanitizer housing having surrounding, enclosing walls including a back wall and a front wall and being of a size enabling easy carry by one hand of a user,
a portable, rechargeable electrical power source;
a source of UV light mounted to the housing, for radiating a target surface spaced from the housing at which it may be directed, with sufficient intensity to kill or otherwise disable any pathogenic viruses or bacteria that may be on the target surface, if and when the target surface is within a maximum effective distance range of the UV light source;
an energization switch for connecting the portable power source to the UV light source;
means for sensing at least one characteristic of the target surface at which the UV light source is directed;
a user control switch;
a microprocessor controller powered by the portable power source for controlling the energization switch to selectively energize the UV light source with the power source
in response to the user control switch, and
in automatic response to the at least one characteristic of the target sensed by the target characteristic sensing means;
the energization switch enabling the user to alternatively energize the UV light source in either a skin surface sanitization mode or a non-skin surface sanitization mode, and including
means only responsive to energization in the skin surface sanitization mode to actuate means for reducing any risk of unsafe, excessive UV light radiation of a person's skin.

30. The personal, portable UV light sanitizer of claim 29 in which the risk reducing means includes at least one of the following excessive radiation risks reducing means of
means to automatically terminate energization of the UV light source after lapse of a preselected maximum safe cycle time period,
means for preventing, during a preselected radiation past accumulation time period, skin radiation time more than a preselected maximum total time of radiation or more than a preselected maximum number of radiation cycles,
means for preventing energization if less than a preselected time period has passed since the end of an immediately prior successive radiation cycle,
means for automatically terminating energization of the UV light source a preselected time after initiation of energization,
means for automatically deenergizing the UV light source if the distance from the light source to the target skin is less than a preselected minimum, and
means for controlling the intensity of UV light radiation depending upon the distance between the UV light source and the target skin, and
means for providing a signal to the user when distance between the UV light source and the skin surface target is less than a preselected minimum.

31. The personal, portable UV light sanitizer of claim 30 in which at least two, at least three, at least three, at least four, at least five or all of the risk reducing means are provided.

32. The personal, portable UV light sanitizer of claim 29 including means for automatically deenergizing the UV light source when in the non-skin surface sanitization mode, if a person's skin is detected as the target surface at which the UV light source is directed.

\* \* \* \* \*